(12) United States Patent
Chang et al.

(10) Patent No.: US 12,241,902 B2
(45) Date of Patent: Mar. 4, 2025

(54) PROBES FOR DETECTION OF COPPER

(71) Applicant: The Regents of the University of California, Oakland, CA (US)

(72) Inventors: Christopher J. Chang, Berkeley, CA (US); Yik Sham Clive Chung, Berkeley, CA (US); Sumin Lee, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 814 days.

(21) Appl. No.: 17/603,205

(22) PCT Filed: Apr. 29, 2020

(86) PCT No.: PCT/US2020/030492
§ 371 (c)(1),
(2) Date: Oct. 12, 2021

(87) PCT Pub. No.: WO2020/226972
PCT Pub. Date: Nov. 12, 2020

(65) Prior Publication Data
US 2022/0196685 A1   Jun. 23, 2022

Related U.S. Application Data

(60) Provisional application No. 62/845,108, filed on May 8, 2019.

(51) Int. Cl.
*G01N 33/84* (2006.01)
*C07D 405/14* (2006.01)

(52) U.S. Cl.
CPC .......... *G01N 33/84* (2013.01); *C07D 405/14* (2013.01)

(58) Field of Classification Search
None
See application file for complete search history.

(56) References Cited

U.S. PATENT DOCUMENTS

| 8,865,914 B2 | 10/2014 | Chang et al. |
| 2009/0253161 A1 | 10/2009 | Franz et al. |
| 2014/0051863 A1 | 2/2014 | Chang et al. |

OTHER PUBLICATIONS

Hu, et al.; "A facile 'click' reaction to fabricate a FRET-based ratiometric fluorescent $Cu^{2+}$ probe"; Journal of Materials Chemistry B; vol. 2, pp. 4467-4472 (Apr. 29, 2014).
Taki, et al.; "Development of highly sensitive fluorescent probes for detection of intracellular copper(I) in living systems"; J. Am. Chem. Soc.; vol. 132, pp. 5938-5939 (Apr. 8, 2010).
Yuan, et al.; "FRET-Based Small-Molecule Fluorescent Probes: Rational Design and Bioimaging Applications"; Accounts of Chemical Research; vol. 46, No. 7, pp. 1462-1473 (Feb. 18, 2013).

*Primary Examiner* — Xiaoyun R Xu
(74) *Attorney, Agent, or Firm* — Rudy J. Ng; Bozicevic, Field & Francis LLP

(57) ABSTRACT

The present disclosure provides Forster resonance energy transfer (FRET)-based probes for detecting copper, e.g., for detecting Cu(I) in live cells. The present disclosure provides methods for detecting copper, e.g., for detecting Cu(I) in live cells, using a FRET-based probe of the present disclosure.

20 Claims, 18 Drawing Sheets

A

B

PROBES FOR DETECTION OF COPPER

CROSS-REFERENCE

This application is a national stage filing under 35 U.S.C. § 371 of PCT/US2020/030492, filed on Apr. 29, 2020, which claims the benefit of U.S. Provisional Patent Application No. 62/845,108, filed May 8, 2019, which applications are incorporated herein by reference in their entirety.

STATEMENT REGARDING FEDERALLY SPONSORED RESEARCH

This invention was made with government support under Grant No. GM079465 awarded by the National Institutes of Health. The government has certain rights in the invention.

INTRODUCTION

Copper is a required redox-active nutrient for life, serving as a potent catalytic and/or structural cofactor in proteins for fundamental processes such as oxygen transport, respiration and metabolism, cell growth and differentiation, and signal transduction. In addition to tightly-bound copper pools buried within metalloprotein active sites, emerging data suggest the presence of labile copper pools that are bound relatively weakly by low molecular weight ligands. Labile copper pools contribute to a growing number of dynamic transition metal signaling pathways including neural communication, olfaction, lipolysis, rest-activity cycles, and kinase pathways involved in signal transduction and oncogenesis. Indeed, copper dysregulation can result in aberrant oxidative and nitrosative stress events that accompany diseases spanning cancer, cardiovascular disorders, neurodegenerative Alzheimer's, Parkinson's and Huntington's diseases, diabetes and obesity, and genetic Menkes and Wilson disorders.

There is a need in the art for compositions and methods for detecting copper in live cells.

SUMMARY

The present disclosure provides Förster resonance energy transfer (FRET)-based probes for detecting copper, e.g., for detecting Cu(I) in live cells. The present disclosure provides methods for detecting copper, e.g., for detecting Cu(I) in live cells, using a FRET-based probe of the present disclosure.

DEFINITIONS

Figure 1:
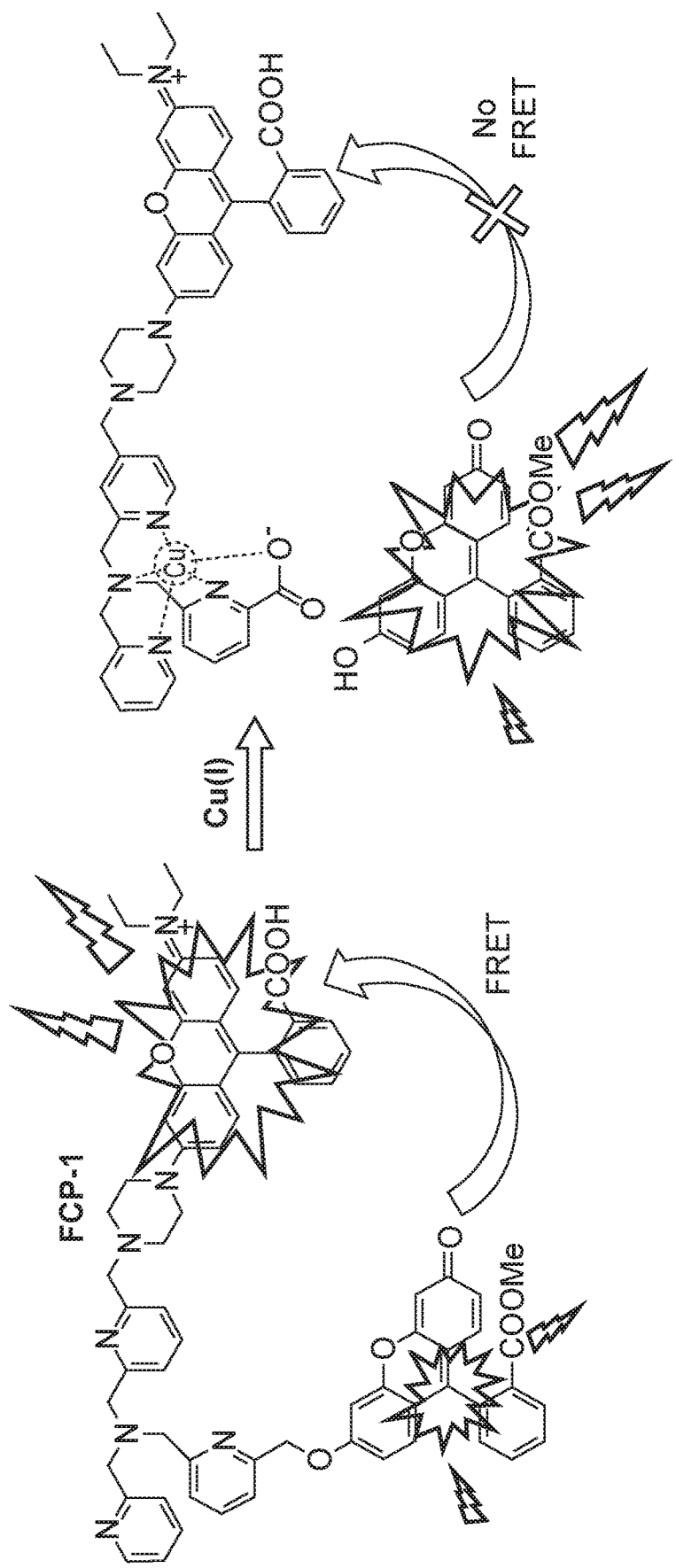
FIG. 1 shows the chemical structure and design of FRET Copper Probe-1, FCP-1.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general, a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" is meant to include an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, may contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated C$_3$-C$_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, C$_1$-C$_8$ alkoxy, C$_1$-C$_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—CH$_2$—), ethylene (—CH$_2$CH$_2$—), propylene (—CH$_2$CH$_2$CH$_2$—), 2-methylpropylene (—CH$_2$—CH(CH$_3$)—CH$_2$—), hexylene (—(CH$_2$)$_6$—) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

"Carboxyl," "carboxy" or "carboxylate" refers to —CO$_2$H or salts thereof.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

As used herein, the terms "Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

"Sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cylcoalkyl, $SO_2$-cycloalkenyl, $SO_2$-substituted cylcoalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

By the term "functional groups" is meant chemical groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH2), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH2), carbamido (—NH—(CO)—NH2), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—NH2), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-($C_1$-$C_{24}$ alkyl)-substituted phosphino, mono- and di-($C_5$-$C_{20}$ aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a bivalent radical moiety that connects two groups via one or more covalent bonds. Examples of such linking groups include alkylene, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH$_2$)n-O—), epoxyimino (—O—NH—), epimino (—NH—), carbonyl (—CO—), etc.

Any convenient orientation and/or connections of the linkers to the linked groups may be used. In some cases, the linker does not include chemical elements but rather is a covalent bond.

When the term "substituted" appears prior to a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)PR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —SR$^{70}$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^7$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

As used herein, the term "Förster resonance energy transfer (FRET) donor group" is used interchangeable with "donor" to refer to a group that is capable of absorbing light energy and then transferring at least some of such light energy to a FRET acceptor group.

As used herein, the term "Förster resonance energy transfer (FRET) acceptor group" is used interchangeable with "acceptor" to refer to a group that is capable of receiving or absorbing energy transferred from a FRET donor group and converting at least some of the transferred energy to emitted light.

As used herein, the terms "excitation spectrum" and "absorption spectrum" are used interchangeably to refers to the ability of a group to absorb and be excited by electromagnetic radiation as a function of the wavelength of the electromagnetic radiation. While the ability to absorb electromagnetic radiation can be measured using various units, the term "normalized excitation spectrum" refers to an excitation spectrum with arbitrary units versus wavelength.

As used herein, the term "emission spectrum" is used to refer to the relative emission of photons, as a function of wavelength, of an excited group. While the amount of electromagnetic radiation emitted can be measured using various units, the term "normalized emission spectrum" refers to an emission spectrum with arbitrary units versus wavelength.

As used herein, the term "FRET emissions" refers to emissions of electromagnetic radiation from an acceptor group based on the Förster resonance energy transfer (FRET) to the acceptor from a donor.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a ratiometric, activity-based FRET probe" includes a plurality of such probes and reference to "the cell" includes reference to one or more cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides ratiometric Förster resonance energy transfer (FRET)-based probes for detecting copper, e.g., for detecting Cu(I) in live cells. The present disclosure provides methods for detecting copper, e.g., for detecting Cu(I) in live cells, using a FRET-based probe of the present disclosure.

FRET-Based Probes

The present disclosure provides compounds and methods of detecting and quantifying Cu(I) in a sample by contacting the sample with an activity-based Förster resonance energy transfer (FRET) probe compound and measuring changes in FRET emissions from the probe.

The activity-based FRET probe is configured such that interacting with Cu(I) will change the FRET emissions of the probe by changing the distance between the FRET donor group and the FRET acceptor group of the probe. In some cases, the change in distance involves cleavage of a covalent bond, e.g. such that the donor and acceptor groups are thereafter part of two separate molecules. In some cases, the change in distance does not involve cleavage of a covalent bond nor separation of the donor and acceptor groups into different molecules.

The present disclosure provides methods of detecting and quantifying Cu(I) that include ratiometric FRET measurements, e.g. measuring the FRET emissions ratio. As used herein, the term "FRET emissions ratio" refers to the ratio between emissions corresponding to a FRET donor and emissions corresponding to a FRET acceptor. The emissions corresponding to each FRET group can be measured either at a particular wavelength or as a range of wavelengths. As such, by changing the distance between the donor and acceptor groups, Cu(I) will also cause a detectable change in the FRET emissions ratio. Thus, the presence and quantity of Cu(I) in a sample can be measured by measuring changes in the FRET emissions ratio.

As an example, an activity-based FRET probe compound, before being contacted with Cu(I), can be exposed to light of a wavelength that excites the donor group of the acceptor, e.g. light of wavelength close to the excitation maximum of the donor. Due to Förster resonance energy transfer from the donor to the acceptor, the fluorescent light emitted by the probe compound will include emissions from the acceptor, i.e. fluorescent light corresponding to the emissions spectrum of the acceptor. The fluorescent emissions can include other light, e.g. light corresponding to the emission spectrum of the donor. However, contact between the probe compound and Cu(I) will cause a change in the distance between the donor and the acceptor, e.g. an increase in distance due to cleavable of a covalent bond linking the donor and the acceptor. Without intending to be limited by theory, if the distance between the donor and the acceptor increases, the magnitude of Förster resonance energy transfer from the donor to the acceptor will decrease, i.e. the intramolecular FRET efficiency will decrease. Thus, there will be a decrease in the amount of emissions corresponding to the emissions spectrum of the acceptor. In some cases, there will be an increase in the amount of emissions corresponding to the emissions spectrum of the donor. Hence, there will be an increase in the FRET emissions ratio, i.e. the ratio between the fluorescent emissions corresponding to the emissions spectrum of the donor and the emissions spectrum of the acceptor. Thus, the FRET emissions ratio can be used to detect or quantify Cu(I) in a sample.

In addition, the methods provided by the disclosure allow for detecting and quantifying Cu(I) in a sample without the need to calibrate for the thickness of the sample, the concentration of the activity-based FRET probe compound, probe uptake, or the intensity of light used to excite the probe compound. As such, the probe compounds are sometimes described herein as self-calibrating. Thus, the disclosure provides methods for accurately comparing the quantity of Cu(I) in a first sample with the quantity of Cu(I) in a second sample without the need for calibrating for any differences in sample thickness, differences in probe compound concentration, differences in probe uptake, or differences in excitation light intensity between the measurements of the two samples. In some cases, the present methods allow for accurate detecting and quantifying without the need to calibrate for self-quenching, i.e. wherein emissions from a probe compound decrease due to being quenched by another probe compound, e.g. a higher concentrations of probe compound.

In some cases, the sample comprises a cell, e.g. a live cell. In some cases, the method involves detecting and quantifying Cu(I) that reacts with the activity-based probe compound, e.g. Cu(I) in labile copper pools, such that Cu(I) in the sample that does not react with the activity-based probe compound, e.g. Cu(I) in tightly-bound copper pools, is not detected or quantified. As such, in some cases, the methods allow accurate measurements of Cu(I) in labile copper pools. In some cases, the Cu(I) in tightly-bound copper pools is Cu(I) in contact with a metalloprotein active site.

The disclosure provides methods of measuring changes in the concentration of Cu(I) in a sample over a period of time. Such methods include measuring Cu(I) concentration at a first time and at a second time.

Figure 12:
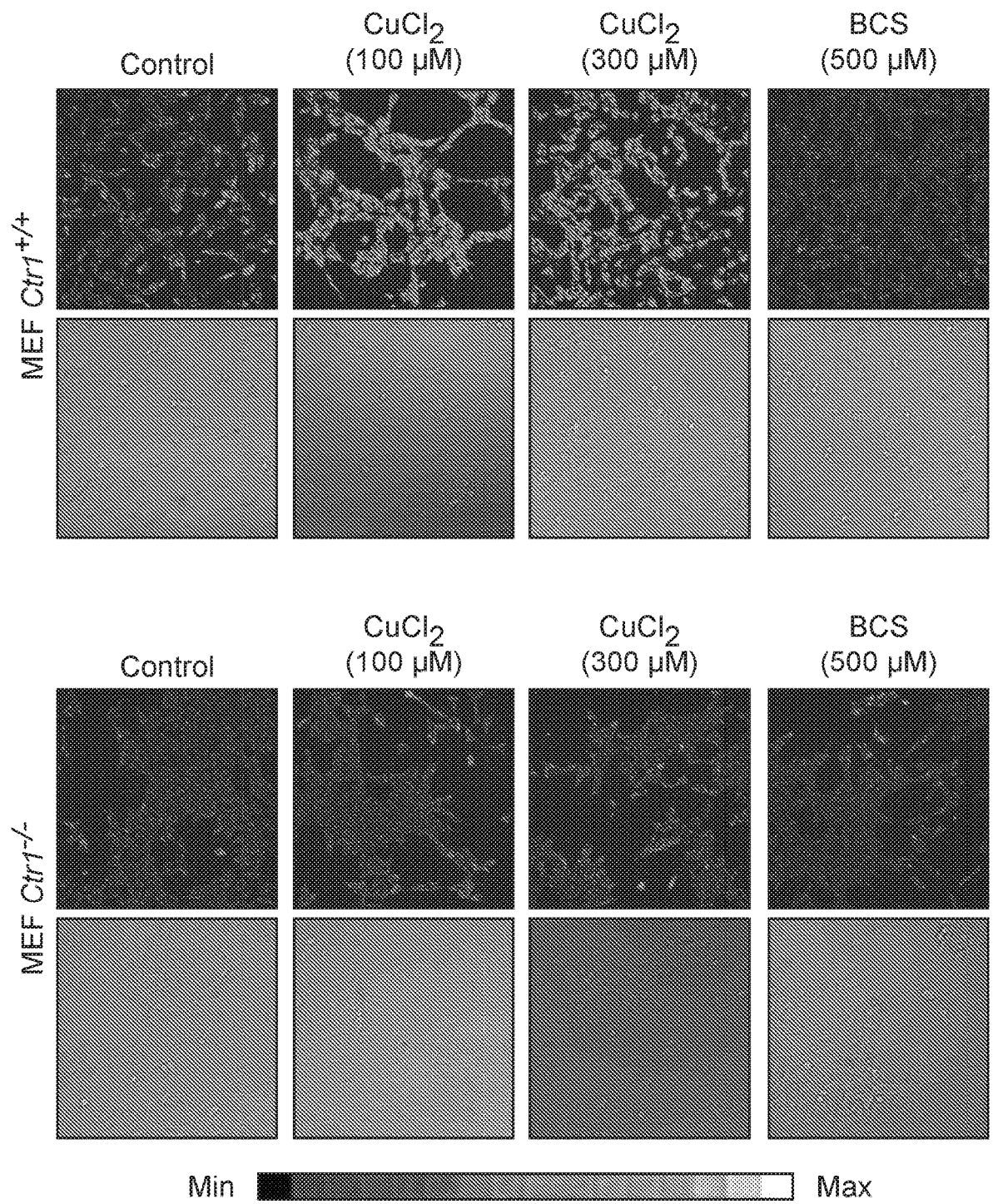
FIG. 12 shows FCP-1 Enables Comparative Imaging of Labile Cu(I) Levels in Live cells With Altered Expression Levels of the High-Affinity Copper Uptake Protein CTR1. (A) Confocal fluorescence microscopy images of Ctr1$^{+/+}$ MEFs and Ctrl$^{-/-}$ MEFs treated with solvent control, CuCl$_2$ (100 or 300 µM) or BCS (500 µM) in complete medium for 8 h, washed with complete medium and PBS, incubated with FCP-1 (5 µM) in DPBS for 45 min, and then imaged with $\lambda_{ex}$=458 nm. (B) Average cellular ratiometric emission ratios of FCP-1, $F_{green}/F_{orange}$, as determined from experiments performed in triplicate. (C) Total cellular $^{63}$Cu levels were determined by ICP-MS experiments (with normalization of different cell numbers by total cellular $^{31}$P level). (D) Confocal fluorescence microscopy images of Ctrl$^{+/+}$ MEFs and Ctrl$^{-/-}$ MEFs incubated with FL-TPA (5 µM) in DPBS for 45 min. The cells were then imaged with $\lambda_{ex}$=488 nm. (E) Average cellular fluorescence intensity of FL-TPA, $F_{FL-TPA}$, determined from experiments performed in triplicate with $\lambda_{ex}$=488 nm. Error bars denote SD (n=3). *p<0.05, p<0.01 and *p<0.001.
Figure 12:
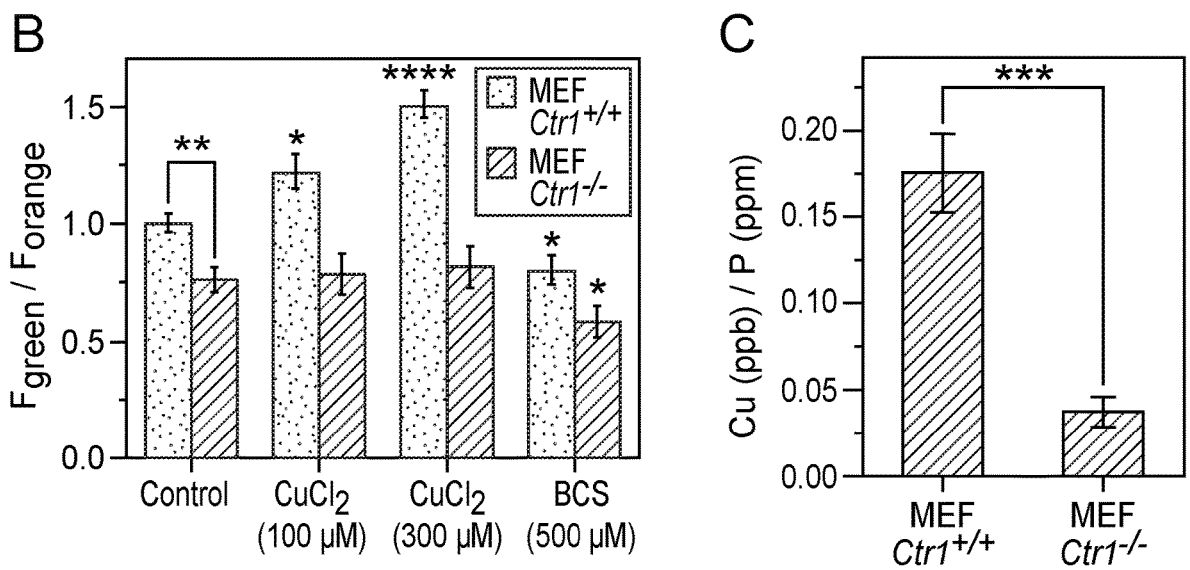
Figure 12:
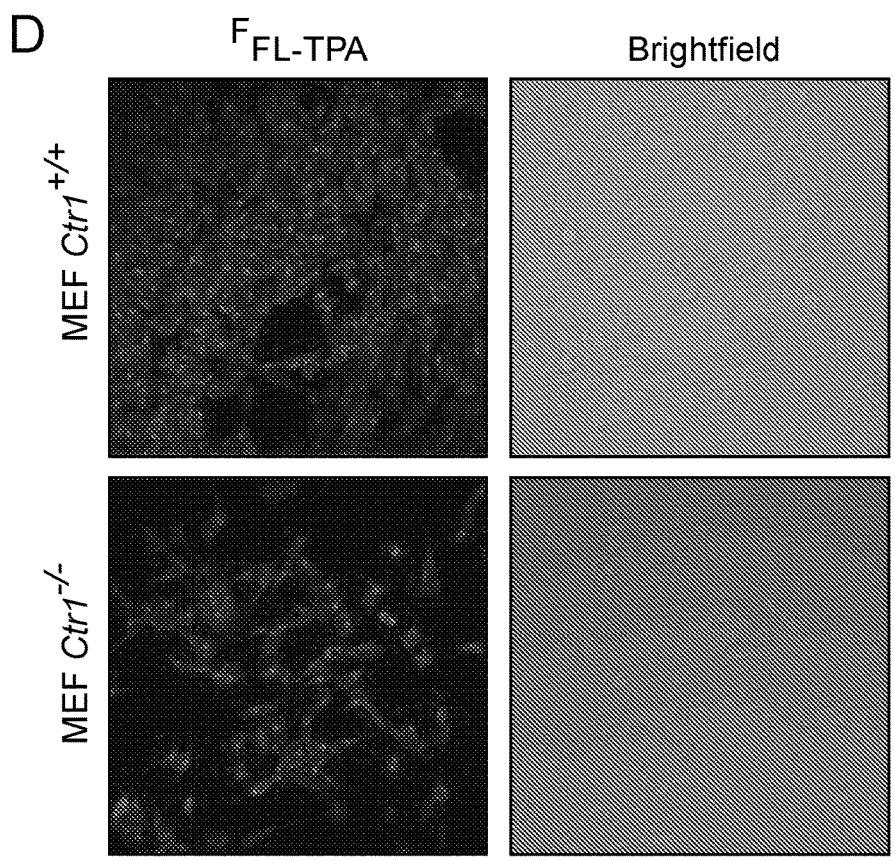
Figure 12:
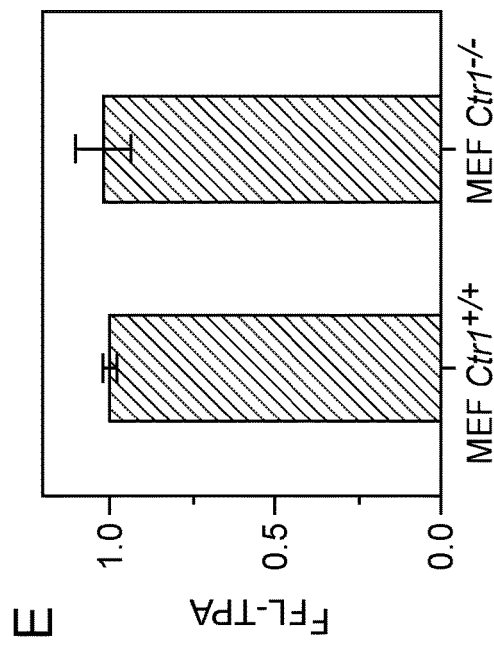

In some cases, measuring the emitted fluorescent light involves capturing a two-dimensional picture of the sample, e.g. so that the emissions from each of multiple cells in a sample can be separately assessed. An example of such capturing is shown in FIG. 12, panel A, which shows images of the fluorescent emissions from multiple cells of different types. Thus, FIG. 12, panel A shows how the color and intensity of the emissions of each cell can be separately measured. In other cases, measuring the emitted fluorescent light involves measuring the light emitted from the sample as a whole, e.g. a single value for all light of a certain wavelength by the sample, or a plot of the intensity of light from the sample as a function of wavelength.

The change in FRET ratio after coordination of Cu(I) is generally close to proportional to the concentration of Cu(I) in the sample. In some cases, the change in FRET ratio can be within 50% of being proportional to the concentration of Cu(I), such as within 40%, within 30%, within 20%, within 10%, within 5%, or within 1%.

Compounds

The present disclosure provides activity-based probe compounds useful in performing the methods described herein.

In some cases, the activity-based probe compound is of the formula (I):

A-X1-E-X2-D    (I)

wherein:
A is a Förster resonance energy transfer (FRET) acceptor group,
D is a FRET donor group,
E is a Cu(I)-coordinating group,
X1 and X2 are linking groups.

As shown in formula (I), each of the groups are connected by covalent bonds. A is covalently bonded to X1, X1 is covalently bonded to E, and X2 is covalently bonded to D. In cases wherein X1 is a covalent bond, A and E are directly covalently bonded. In cases wherein X2 is a covalent bond, E and D are directly covalently bonded.

As described above, in some cases one or more linking groups can be cleaved by Cu(I). As such, in some cases, X1 is cleavable by Cu(I) but X2 is not cleavable by Cu(I). Thus, in cases wherein X1 is cleaved by Cu(I), such cleavage causes A and E to no longer be covalently bonded to one another. Similarly, in cases wherein X2 is cleaved by Cu(I), such cleavage causes E and D to no longer be covalently bonded to one another.

In addition, the activity-based probe compound is configured such that Förster resonance energy transfer from D to A is possible. Without being limited by theory, it is thought such FRET efficiency depends upon the distance between D and A. As such, the probe compound is configured such that D and A are located within a distance of each other such that Förster resonance energy transfer from D to A is possible, e.g. 1% or more of energy absorbed by D is transferred to D, such as 5% or more, 10% or more, 20% or more, 30% or more, 50% or more, or 75% or more.

In some cases, the coordination of Cu(I) to E causes a change in FRET efficiency without causing the cleavage of a bond. In such cases, such coordination causes a change in the distance between D and A, e.g. an increase of 5% or more, such as 10% or more, 15% or more, 20% or more, 30% or more, 50% or more, or 100% or more. Such an increase in distance can be caused by a conformational change in E, e.g. the coordination of nitrogen groups of E to Cu(I) as shown in FIG. 1.

Groups X1 and X2

In some cases, X1, X2, or both X1 and X2 are cleavable by Cu(I). In some cases, X1 is cleavable by Cu(I) and X2 is not cleavable by Cu(I). In some cases, X2 is cleavable by Cu(I) and X1 is not cleavable by Cu(I). In some cases, both X1 and X2 are cleavable by Cu(I).

As used herein, the cleavage of X1 by Cu(I) refers to not only the cleavage of a covalent bond within X1, but also the cleavage of a covalent bond that connects X1 to A or a covalent bond that connects X1 to E. Similarly, the cleavage of X2 by Cu(I) refers to not only the cleavage of a covalent bond within X2, but also the cleavable of a covalent bond that connects X2 to E or a covalent bond that connects X2 to D.

In some cases, X1 comprises a C—O bond cleavable by Cu(I). Stated in another manner, there is a C—O bond within X1 that is cleavable by Cu(I). In some cases, X2 comprises a C—O bond cleavable by Cu(I). Stated in another manner, there is a C—O bond within X2 that is cleavable by Cu(I). In some cases, at least one of X1 and X2 comprise a C—O bond cleavable by Cu(I).

In some cases, the connection between X1 and A is a C—O bond, e.g. wherein the oxygen atom is a part of X1 and the carbon atom is a part of A. In some cases, such a bond is cleavable by Cu(I), i.e. X1 is cleavable by Cu(I), as described above. Thus, in such cases, the A-X1 moiety comprises a C—O bond that is cleavable by Cu(I).

Similarly, in some cases, the connection between X2 and D is a C—O bond, e.g. wherein the oxygen atom is a part of X2 and the carbon atom is a part of D. In some cases, such a bond is cleavable by Cu(I), i.e. X2 is cleavable by Cu(I), as described above. Thus, in such cases, the X2-D moiety comprises a C—O bond that is cleavable by Cu(I).

In some cases, the X1-E moiety comprises a C—O bond cleavable by Cu(I). In some cases, the X2-E moiety comprises a C—O bond cleavable by Cu(I).

In some cases, at least one of A-X1 moiety and X2-D moiety comprise the structure of formula (II):

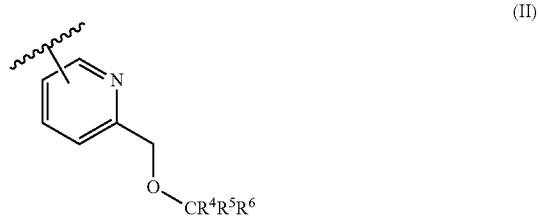

wherein a C—O group of formula (II) is cleavable by Cu(I),
wherein $R^4$, $R^5$, and $R^6$ are each independently selected from H or a hydrocarbon group.

In some embodiments of formula (II), the $CH_2$—O bond is cleavable by Cu(I). As such, in cases wherein the pyridyl-$CH_2$—O group is part of X1, e.g. and $CR^4R^5R^6$ is part of A, X1 comprises a group cleavable by Cu(I). Similarly, in cases wherein the pyridyl-$CH_2$—O group is part of X2, e.g. and $CR^4R^5R^6$ is part of D, X2 comprises a group cleavable by Cu(I).

In some cases, at least one of A-X1 moiety and X2-D moiety comprise the structure of formula (III):

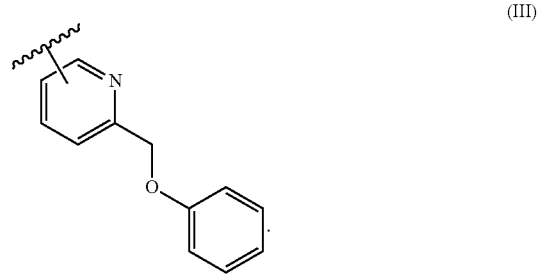

In some cases, the A-X1 moiety comprises a C—N bond cleavable by Cu(I). In some cases, the X2-D moiety comprises a C—N bond cleavable by Cu(I). In some cases, at least one of the A-X1 and X2-D moiety comprise a C—N bond cleavable by Cu(I).

In some cases, neither X1 nor X2 are cleavable by Cu(I). In such cases, E is configured such that coordination of Cu(I) to E will cause a change in a distance between the acceptor and the donor. In such cases, such coordination causes a change in the distance between D and A, e.g. an increase of 5% or more, such as 10% or more, 15% or more, 20% or more, 30% or more, 50% or more, or 100% or more. Such an increase in distance can be caused by a conformational change in E, e.g. the coordination of nitrogen groups of E to Cu(I) as shown in FIG. 1.

Group E

In some cases, E has a formula selected from:

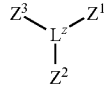  (IV)

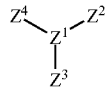  (V)

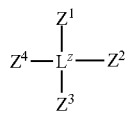  (VI)

(VII)

(VIII)

(IX)

wherein each of $Z^1$, $Z^2$, $Z^3$, and $Z^4$ is independently selected from a coordination group, wherein $L^z$ is a linker, wherein E is a tridentate or tetradentate group.

In some cases, each of $Z^1$, $Z^2$, $Z^3$, and $Z^4$ is independently selected from the group consisting of:

 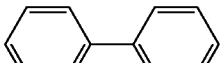

pyridine (pyr)   2,2'-bipyridine(bpy)

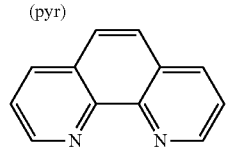

 $NR^1R^2R^3$ amine 1,10-phenathroline (phen)

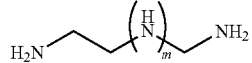

ethylenediamine (en) (m = 0)
diethylenetriamine (m = 1)

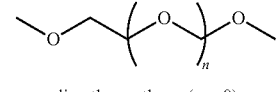 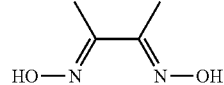

dimethoxyethane (n = 0)
1,2-dimethoxyethane (DME) (n = 1)   dimenthylglyoxime (dgm)

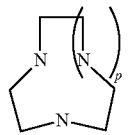  formula (X)

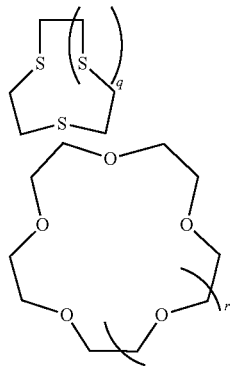

formula (XI)

15-crown-5 (r = 1)
18-crown-6 (r = 2)

a functionalized thioether, an NS4, a cryptand, a cryptate, a clathrochelate, and derivatives and homologs thereof, wherein m is 0 or 1,
n is 0 or 1,
p is 1 or 2,
q is 1 or 2,
r is 1 or 2,
each of $R^1$, $R^2$, and $R^3$ is independently selected from H and an alkyl group.

The denticity of each Z group can be equal to the number of heteroatoms in the Z group. As such, monodentate Z groups include, but are not limited to, pyridine and $NR^1R^2R^3$. Bidentate Z groups include, but are not limited to, 2,2'-bipyridine, 1,10-phenathroline, ethylenediamine, dimethoxyethane, and dimethylglyoxime. Tridentate Z groups include, but are not limited to, diethylenetriamine, 1,2-dimethoxyethane, formula (X) wherein p is 1, formula (XI) wherein q is 1. Tetradenate Z groups include, but are not limited to, formula (X) wherein p is 2, formula (XI) wherein q is 2.

In some cases, E has the formula (VIII). In some of such cases, $Z^1$ is $NR^1R^2R^3$ wherein each of each of R1, R2, and R3 is an alkyl group. In some cases, $Z^2$, $Z^3$, and $Z^4$ are each comprise a pyridine group. In some cases, E comprises the structure (XII):

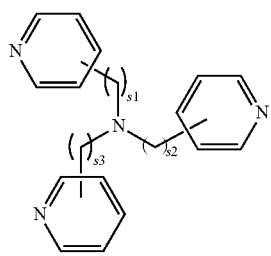  (XII)

wherein s1, s2, and s3 are each independently selected from 0, 1, 2, 3, 4, and 5.

In some embodiments of formula (XII), X1 is attached to a carbon ortho to a pyridyl nitrogen. In some cases, X2 is attached to a carbon ortho to a pyridyl nitrogen. In some cases, X1 and X2 are attached to different pyridyl groups.

In some cases, structure (XII) can be a tridentate group. In some cases (XII) can be a tetradentate group.

In some cases, E comprises the structure (XIII):

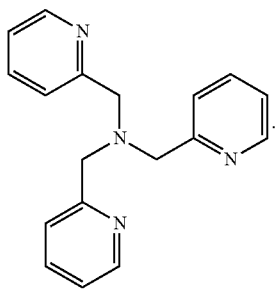

(XIII)

As used herein, the structure (XIII) is also referred to as a tris[(2-pyridyl)methyl]amine (TPA) group.

In some embodiments of formula (XIII), X1 is attached to a carbon ortho to a pyridyl nitrogen. In some cases, X2 is attached to a carbon ortho to a pyridyl nitrogen. In some cases, X1 and X2 are attached to different pyridyl groups.

In some cases, the activity-based probe compound comprises the structure (XIV):

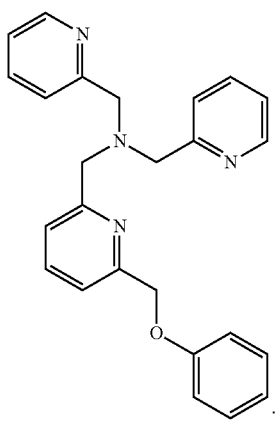

(XIV)

In some cases, E has the formula (VIII) or (IX) and each Z comprises a pyridine group.

In some embodiments of formula (XIV), X1 is attached to a carbon ortho to a pyridyl nitrogen. In some cases, X2 is attached to a carbon ortho to a pyridyl nitrogen. In some cases, X1 and X2 are attached to different pyridyl groups.

In some cases, E has the formula (V), (VI) or (VII) and $Z^1$ is a bidentate group. In some cases, $Z^1$ is selected from 2,2'-bipyridine (bpy), 1,10-phenathroline (phen), ethylene diamine (en), 1,2-dimethoxyethane (DME), and dimethoxyglyoxime (dgm). In some cases, $Z^1$ is selected from a 2,2'-bipyridine (bpy) and 1,10-phenathroline (phen). In some cases, E has the formula (V) and wherein $Z^1$ and $Z^2$ are each a bidentate group. In some cases, $Z^1$ and $Z^2$ are independently selected from 2,2'-bipyridine (bpy) and 1,10-phenathroline (phen).

In some cases, E has the formula (VI) or (VII) or (VIII), or (IX) and at least one Z comprises $NR^1R^2R^3$.

In some cases, E is a group that selectively coordinates to Cu(I), i.e. E preferentially coordinates to Cu(I) relative to one or more other species. In some cases, E preferentially coordinates to Cu(I) relative to one or more other species by a factor of 2 or more, 5 or more, 10 or more, 100 or more, 1,000 or more, or 10,000 or more. In some cases, E is selective for Cu(I) over one or more of iron, cobalt, lithium, sodium, potassium, magnesium, and ions thereof. In some cases, E is selective for Cu(I) over Co(II). As such, the present disclosure provides methods for accurately detecting and quantifying Cu(I) without such measurements being affected by the presence of Co(II).

In some cases, E is selective for Cu(I) over one or more of Cu(II), Cu(III), Cu(IV), and Cu(0). In some cases, E is selective for Cu(I) over Cu(II). As such, the present disclosure provides methods for accurately detecting and quantifying Cu(I) without such measurements being affected by the presence of Cu(II).

In some cases, E has the formula (IV) or (V) and $Z^1$ has the formula (X), (XI), 15-crown-5, 18-crown-6, a functionalized thioether, or NS4.

In some embodiments, E is configured such that coordination of Cu(I) to E will cause a change in a distance between the acceptor and the donor. As such, both X1 and X2 can be groups that are not cleaved by Cu(I). In some cases, E comprises a functionalized thioether. In some cases, the functionalized thioether comprises four nitrogen atoms and one sulfur atom. In some cases, the coordination of Cu(I) to E causes an increase of 10% or more in a distance between A and D, such as 20% or more, 30% or more, 50% or more, 75% or more, or 100% or more. In some cases, the coordination of Cu(I) to E causes a decrease of 10% or more in a distance between A and D, such as 20% or more, 30% or more, 50% or more, 75% or more, or 100% or more.

FRET Acceptor

Various acceptor groups can be used in the activity-based probe compounds described herein. In some cases, the acceptor comprises a moiety selected from the group consisting of a small molecule dye group, a fluorescent protein group, and a quantum dot.

In some cases, the acceptor comprises a small molecule dye group. In some cases, the small molecule dye group is a xanthene, a rhodamine, a fluorescein, a coumarin, a pyrene, a phenanthridine, a boron difluoride dipyrromethene (BODIPY), a cyanine, a phthalocyanine, an oxazine, an acridine, a fluorone, or derivatives thereof. In some cases, the small molecule dye is a rhodamine, e.g. rhodamine B.

In some cases, the acceptor comprises a fluorescent protein group. In some cases, the fluorescent protein group is a green fluorescent protein (GFP) group.

In some cases, the acceptor comprises a quantum dot.

In addition, an acceptor with various optical properties can be used, e.g. an acceptor with a certain excitation maximum, a certain emission maximum, a certain Stoke's shift, or a combination thereof. In some cases, the acceptor has a Stoke's shift of at least 20 nm. In some cases, the acceptor has an excitation maximum between 400 and 700 nm, such as between 450 and 650 nm, between 500 and 600 nm, between 400 and 600 nm, and between 500 and 700 nm.

FRET Donor

Various donor groups can be used in the activity-based probe compounds described herein. In some cases, the donor comprises a moiety selected from the group consisting of a small molecule dye group, a fluorescent protein group, and a quantum dot.

In some cases, the acceptor comprises a small molecule dye group. In some cases, the small molecule dye group is a xanthene, a rhodamine, a fluorescein, a coumarin, a pyrene, a phenanthridine, a boron difluoride dipyrromethene (BODIPY), a cyanine, a phthalocyanine, an oxazine, an acridine, a fluorone, or derivatives thereof. In some cases, the small molecule dye is a fluorescein, e.g. a fluorescein group comprising a methyl ester moiety.

In some cases, the donor comprises a fluorescent protein group. In some cases, the fluorescent protein group is a green fluorescent protein (GFP) group.

In some cases, the donor comprises a quantum dot.

In addition, an acceptor with various optical properties can be used, e.g. an donor with a certain excitation maximum, a certain emission maximum, a certain Stoke's shift, or a combination thereof. In some cases, the donor has a Stoke's shift of at least 20 nm. In some cases, the acceptor has an excitation maximum between 400 and 700 nm, such as between 450 and 650 nm, between 500 and 600 nm, between 400 and 600 nm, and between 500 and 700 nm. In some cases, the acceptor has an excitation maximum between 400 nm and 550 nm, such as between 450 nm and 525 nm. In some cases, the acceptor has an emission maximum between 400 nm and 600 nm, such as between 475 nm and 550 nm.

FRET Pair

The acceptor and the donor are selected based on the relationship between their optical properties. Without intending to be limited by theory, it is thought that the efficiency of the transfer of energy from a FRET donor to a FRET acceptor depends in part upon the overlap between the normalized emission spectrum of the donor and the normalized excitation spectrum of the acceptor. It is thought that more overlap between such spectra results in more efficient FRET energy transfer. In some cases, such an overlap can be 5% or more, such as 10% or more, 20% or more, 50% or more, or 75% or more.

Without intending to be limited by theory, it is thought that the efficiency of the transfer of energy from a FRET donor to a FRET acceptor depends in part upon the distance between the donor and the acceptor. It is thought that a smaller distance between the donor and acceptor results in more efficient FRET energy transfer.

In some cases, the activity-based probe compound has a FRET efficiency of 5% or more, such as 10% or more, 15% or more, 20% or more, 30% or more, 40% or more, 50% or more, or 75% or more.

As described herein, the presence of an analyte of interest, e.g. Cu(I), can be detected and quantified by measuring emitted light, e.g. by comparing the magnitude of emissions at a first wavelength range versus the emissions at a second wavelength range. As described herein, one wavelength range can correspond to emissions from the donor group and the second wavelength range can correspond to emissions from the acceptor group.

As such, in some cases it is desirable to employ donor and acceptor groups to facilitate measurement of this ratio by having donor and acceptor groups with significantly different emission spectra. In some cases, the overlap between the normalized emission spectrum of the donor and the normalized emission spectrum of the acceptor is 75% or less, such as 50% or less, 25% or less, 10% or less, or 5% or less. In some cases, the emission maximum of the donor and the emission maximum of the acceptor are 10 nm or more away from one another, such as 15 nm or more, 20 nm or more, 25 nm or more, 50 nm or more, 75 nm or more, 100 nm or more, or 150 nm or more.

Detection Methods

The disclosure provides methods of detecting and/or quantifying Cu(I) that include ratiometric FRET measurements, e.g. measuring the FRET emissions ratio. As used herein, the term "FRET emissions ratio" refers to the ratio between emissions corresponding to a FRET donor and emissions corresponding to a FRET acceptor. The emissions corresponding to each FRET group can be measured either at a particular wavelength or as a range of wavelengths. As such, by changing the distance between the donor and acceptor groups, Cu(I) will also cause a detectable change in the FRET emissions ratio. Thus, the presence and quantity of Cu(I) in a sample can be measured by measuring changes in the FRET emissions ratio.

A detection method of the present disclosure can be used in various research applications, diagnostic applications, and other applications. A detection method of the present disclosure can also be used in conjunction with (e.g., as a companion diagnostic) a treatment method.

As an example, an activity-based FRET probe compound, before being contacted with Cu(I), can be exposed to light of a wavelength that excites the donor group of the acceptor, e.g. light of wavelength close to the excitation maximum of the donor. Due to Förster resonance energy transfer from the donor to the acceptor, the fluorescent light emitted by the probe compound will include emissions from the acceptor, i.e. fluorescent light corresponding to the emissions spectrum of the acceptor. The fluorescent emissions can include other light, e.g. light corresponding to the emission spectrum of the donor. However, contact between the probe compound and Cu(I) will cause a change in the distance between the donor and the acceptor, e.g. an increase in distance due to cleavable of a covalent bond linking the donor and the acceptor. Without intending to be limited by theory, if the distance between the donor and the acceptor increases, the magnitude of Förster resonance energy transfer from the donor to the acceptor will decrease, i.e. the intramolecular FRET efficiency will decrease. Thus, there will be a decrease in the amount of emissions corresponding to the emissions spectrum of the acceptor. In some cases, there will be an increase in the amount of emissions corresponding to the emissions spectrum of the donor. Hence, there will be an increase in the FRET emissions ratio, i.e. the ratio between the fluorescent emissions corresponding to the emissions spectrum of the donor and the emissions spectrum of the acceptor. Thus, the FRET emissions ratio can be used to detect or quantify Cu(I) in a sample.

In addition, the methods provided by the disclosure allow for detecting and quantifying Cu(I) in a sample without the need to calibrate for the thickness of the sample, the concentration of the activity-based FRET probe compound, probe uptake, or the intensity of light used to excite the probe compound. As such, the probe compounds are sometimes described herein as self-calibrating. Thus, the disclosure provides methods for accurately comparing the quantity of Cu(I) in a first sample with the quantity of Cu(I) in a second sample without the need for calibrating for any differences in sample thickness, differences in probe compound concentration, differences in probe uptake, or differences in excitation light intensity between the measurements of the two samples. In some cases, the present methods allow for accurate detecting and quantifying without the need to calibrate for self-quenching, i.e. wherein emissions from a probe compound decrease due to being quenched by another probe compound, e.g. a higher concentrations of probe compound.

In some cases, the sample comprises a cell, e.g. a live cell. In some cases, the method involves detecting and quantifying Cu(I) that reacts with the activity-based probe compound, e.g. Cu(I) in labile copper pools, such that Cu(I) in the sample that does not react with the activity-based probe compound, e.g. Cu(I) in tightly-bound copper pools, is not detected or quantified. As such, in some cases, the methods allow accurate measurements of Cu(I) in labile copper pools. In some cases, the Cu(I) in tightly-bound copper pools is Cu(I) in contact with a metalloprotein active site.

The disclosure provides methods of measuring changes in the concentration of Cu(I) in a sample over a period of time. Such methods include measuring Cu(I) concentration at a first time and at at least a second time.

A method of the present disclosure for detecting Cu(I) in a living cell comprises: a) contacting the cell with a ratiometric, activity-based FRET probe of the present disclosure; exciting the probe with light, such that the probe undergoes emission; and b) measuring the FRET emissions ratio of the probe. Measuring the FRET emissions ratio of the probe can comprise measuring emission from the probe at a first wavelength and measuring emission from the probe at a second wavelength, where the FRET emissions ratio is the ratio of the emission at the first wavelength to the emission at the second wavelength. In some cases, the first wavelength and the second wavelength differ from one another by at least 50 nm. For example, in some cases, the first wavelength is at least 50 nm (e.g., at least 50 nm, at least 75 nm, at least 100 nm, at least 125 nm, at least 150 nm, or at least 200 nm) longer than the second wavelength. As another example, in some cases, the second wavelength is at least 50 nm (e.g., at least 50 nm, at least 75 nm, at least 100 nm, at least 125 nm, at least 150 nm, or at least 200 nm) longer than the first wavelength. For example, depending on the FRET probe, the ratio of green fluorescence to orange fluorescence ($F_{green}/F_{orange}$) is detected. As another example, in some cases, the ratio of green fluorescence to red fluorescence ($F_{green}/F_{red}$) is detected. In some cases, the cell is in vitro. In some cases, the cell is in vivo. In some cases, a method of the present disclosure detects ratiometric emission over time.

Cells in which Cu(I) can be detected using a method of the present disclosure include mammalian cells, including human cells, non-human primate cells, feline cells, ungulate cells, canine cells, bovine cells, ovine cells, equine cells, etc. Cells in which Cu(I) can be detected using a method of the present disclosure include cells of a reptile, an amphibian, a fish, a bird, etc. Where a method of the present disclosure is carried out in vivo, a method of the present disclosure comprises contacting a cell in an individual with a ratiometric, activity-based FRET probe of the present disclosure. An individual can be a mammal, e.g., a human, a non-human primate, a feline, an ungulate, a canine, an ovine, an equine, etc.

Suitable cells include, e.g., neurons, glial cells, astrocytes, fibroblasts, stem cells (e.g., an adult stem cell, an embryonic stem cell, a somatic stem cell, an adipose-derived stem cell, a stem cell derived from an epithelial cell or tissue, a hematopoietic stem cell, a mammary stem cell, a mesenchymal stem cell, a neural stem cell, an olfactory adult stem cell, a spermatogonial progenitor cell, a dental pulp-derived stem cell, a cancer stem cell), epithelial cells, endothelial cells, blood cells, cells of the immune system, cells of the central nervous system, cells of the peripheral nervous system, dendritic cells, macrophages, muscle cells (e.g., smooth muscle cells; skeletal muscle cells; etc.), epidermal cells, osteoblasts, osteoclasts, retinal cells (e.g., Müller cells), lymphocytes, cardiac cells, liver cells (e.g., hepatocytes), pancreatic cells (e.g., beta islet cells), melanocytes, adipocytes, keratinocytes, mucosal cells, bone cells, chondrocytes, etc. Blood cells include, e.g., T cells, B cells, natural killer cells, and the like.

In carrying out a method of the present disclosure, a ratiometric FRET probe of the present disclosure can be administered directly into a tissue or organ. For example, a ratiometric FRET probe of the present disclosure can be administered directly into a tumor, a liver, a kidney, a pancreas, a heart, a nerve tissue, muscle, a blood tissue, bone, skin, eye, or other tissue or organ.

In some cases, a method of the present disclosure comprises: a) detecting a level of Cu(I) in a diseased cell; and b) detecting a level of Cu(I) in a non-diseased cell of the same cell type as the diseased cell. Where the level of Cu(I) in the diseased cell is significantly lower in the diseased cell, compared with the control, non-diseased cell of the same cell type, indicates labile Cu(I) deficiency in the diseased cell. In some cases, the diseased cell is a cancerous cell.

In some cases, a method of the present disclosure comprises: a) administering a ratiometric FRET probe of the present disclosure to an individual having a disease (where the administering is systemic; or where the administering is at, near, or into a diseased tissue or organ in the individual); and b) measuring the FRET emissions ratio of the probe. In some cases, the disease is selected from a cancer, a cardiovascular disorder, Alzheimer's disease, Parkinson's disease, Huntington's disease, diabetes, obesity, Menkes disease, and Wilson's disease.

A method of the present disclosure can be used to image dynamic changes in labile Cu(I) pools in live cells in response to various conditions. Such conditions include, e.g., copper supplementation, copper depletion, differential expression of the copper importer CTR1, and redox stress (oxidative stress).

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-58 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A compound of the formula (I):

$$A\text{-}X1\text{-}E\text{-}X2\text{-}D \qquad (I)$$

wherein:

A is a Förster resonance energy transfer (FRET) acceptor group,

D is a FRET donor group,

E is a Cu(I)-coordinating group,

X1 and X2 are linking groups.

Aspect 2. The compound of Aspect 1, wherein X1, X2, or both X1 and X2, are cleavable by Cu(I).

Aspect 3. The compound of Aspect 2, wherein X1 and not X2 is cleavable by Cu(I).

Aspect 4. The compound of Aspect 2, wherein X2 and not X1 is cleavable by Cu(I).

Aspect 5. The compound of Aspect 2, wherein at least one of the A-X1 moiety and the X2-D moiety comprises a C—O bond cleavable by Cu(I).

Aspect 6. The compound of Aspect 5, wherein the compound comprises the structure of formula (II):

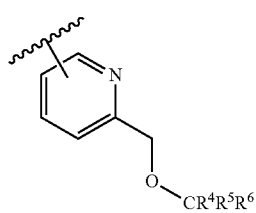

(II)

wherein a C—O group of formula (II) is cleavable by Cu(I),
wherein $R^4$, $R^5$, and $R^6$ are each independently selected from H or a hydrocarbon group.

Aspect 7. The compound of Aspect 6, wherein the compound comprises the structure of formula (III):

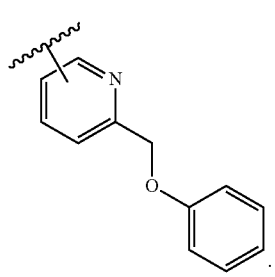

(III)

Aspect 8. The compound of Aspect 2, wherein at least one of the A-X1 moiety and the X2-D moiety comprises a C—N bond cleavable by Cu(I).

Aspect 9. The compound of Aspect 1, wherein E has a formula selected from:

$Z^1$ (IV)

$Z^1—Z^2$ (V)

$Z^1—Z^2—Z^3$ (VI)

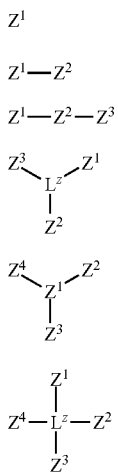

(VII)

(VIII)

(IX)

wherein each Z is a coordination group,
wherein $L^z$ is a linker,
wherein E is a tridentate or tetradentate group.

Aspect 10. The compound of Aspect 9, wherein each Z is independently selected from:

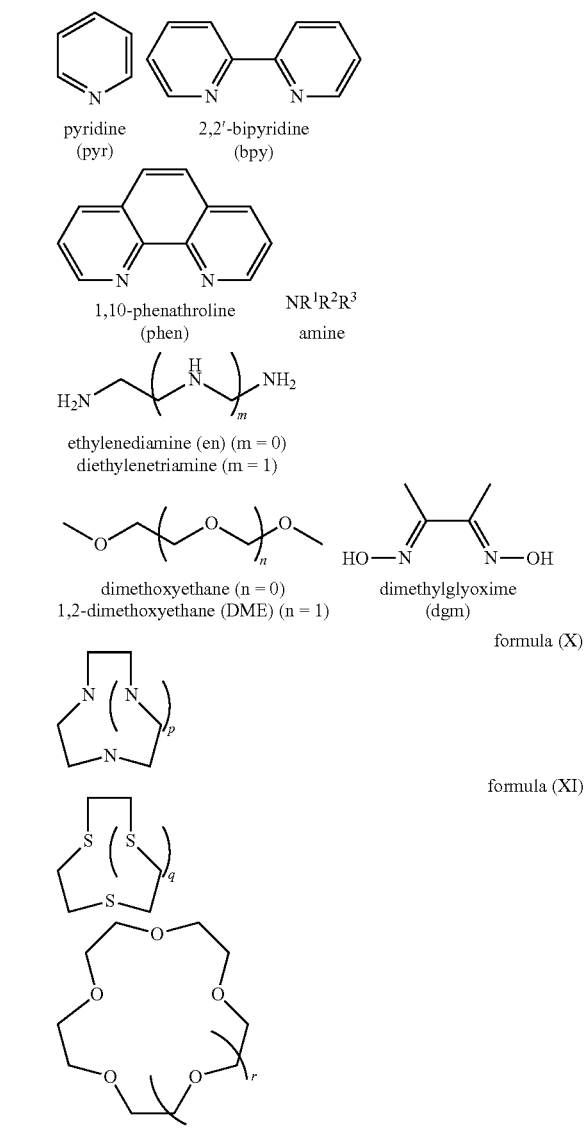

a functionalized thioether, and derivatives and homologs thereof,
wherein m is 0 or 1,
wherein n is 0 or 1,
wherein p is 1 or 2,
wherein q is 1 or 2,
wherein r is 1 or 2,
wherein each of $R^1$, $R^2$, and $R^3$ are independently selected from H and an alkyl group, Aspect 11. The compound of Aspect 9, wherein E has the formula (VIII).

Aspect 12. The compound of Aspect 11, wherein $Z^1$ is $NR^1R^2R^3$ and wherein each of $R^1$, $R^2$, and $R^3$ is an alkyl group.

Aspect 13. The compound of Aspect 12, wherein $Z^2$, $Z^3$, and $Z^4$ are each comprise a pyridine group.

Aspect 14. The compound of Aspect 13, wherein E comprises the structure (XII):

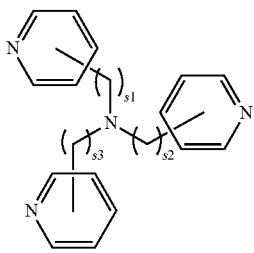

(XII)

wherein s1, s2, and s3 are each independently selected from 0, 1, 2, 3, 4, and 5.

Aspect 15. The compound of Aspect 14, wherein E comprises the structure (XIII):

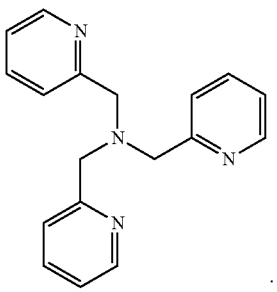

(XIII)

Aspect 16. The compound of Aspect 15, wherein the composition comprises the structure (XIV):

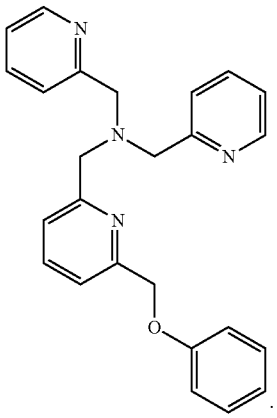

(XIV)

Aspect 17. The composition of Aspect 9, wherein E has the formula (VIII) or (IX) and each Z comprises a pyridine group.

Aspect 18. The composition of Aspect 9, wherein E has the formula (V), (VI) or (VII) and $Z^1$ is a bidentate group.

Aspect 19. The compound of Aspect 18, wherein $Z^1$ is selected from 2,2'-bipyridine (bpy), 1,10-phenathroline (phen), ethylene diamine (en), 1,2-dimethoxyethane (DME), and dimethoxyglyoxime (dgm).

Aspect 20. The compound of Aspect 19, wherein $Z^1$ is selected from a 2,2'-bipyridine (bpy) and 1,10-phenathroline (phen).

Aspect 21. The compound of Aspect 9, wherein E has the formula (V) and wherein $Z^1$ and $Z^2$ are each a bidentate group.

Aspect 22. The compound of Aspect 21, wherein $Z^1$ and $Z^2$ are independently selected from 2,2'-bipyridine (bpy) and 1,10-phenathroline (phen).

Aspect 23. The compound of Aspect 9, wherein E has the formula (VI) or (VII) or (VIII), or (IX), and wherein at least one Z comprises $NR^1R^2R^3$.

Aspect 24. The compound of Aspect 9, wherein E has the formula (IV) or (V), and wherein $Z^1$ has the formula (X), (XI), 15-crown-5, 18-crown-6, or a functionalized thioether.

Aspect 25. The compound of Aspect 1, wherein coordination of Cu(I) to E causes a change in a distance between A and D.

Aspect 26. The compound of Aspect 25, wherein coordination of Cu(I) to E causes an increase of 10% or more or a decrease of 10% or more in a distance between A and D.

Aspect 27. The compound of Aspect 1, wherein A comprises a small molecule dye group.

Aspect 28. The compound of Aspect 27, wherein A comprises a rhodamine group.

Aspect 29. The compound of Aspect 28, wherein A comprises a rhodamine B group.

Aspect 30. The compound of Aspect 1, wherein A has an excitation maximum between 500 nm and 600 nm.

Aspect 31. The compound of Aspect 1, wherein A has a Stoke's shift of at least 20 nm.

Aspect 32. The compound of Aspect 1, wherein A comprises a fluorescent protein group.

Aspect 33. The compound of Aspect 32, wherein A comprises a green fluorescent protein (GFP) group.

Aspect 34. The compound of Aspect 1, wherein A comprises a quantum dot.

Aspect 35. The compound of Aspect 1, wherein D comprises a small molecule dye group.

Aspect 36. The compound of Aspect 35, wherein D comprises a fluorescein group.

Aspect 37. The compound of Aspect 36, wherein D comprises a fluorescein group comprising a methyl ester.

Aspect 38. The compound of Aspect 1, wherein D has an excitation maximum between 450 nm and 525 nm.

Aspect 39. The compound of Aspect 1, wherein D has an emission maximum between 475 nm and 550 nm.

Aspect 40. The compound of Aspect 1, wherein A has a Stoke's shift of at least 20 nm.

Aspect 41. The compound of Aspect 1, wherein D comprises a fluorescent protein group.

Aspect 42. The compound of Aspect 41, wherein D comprises a green fluorescent protein (GFP) group.

Aspect 43. The compound of Aspect 1, wherein D comprises a quantum dot.

Aspect 44. The compound of Aspect 1, wherein the overlap between the normalized emission spectrum of D and the normalized excitation spectrum of A is 10% or more.

Aspect 45. The compound of Aspect 1, wherein the overlap between the normalized emission spectrum of D and the normalized excitation spectrum of A is 50% or more.

Aspect 46. The compound of Aspect 1, wherein the compound has a FRET efficiency of 10% or more.

Aspect 47. The compound of Aspect 1, wherein the compound has a FRET efficiency of 50% or more.

Aspect 48. The compound of Aspect 1, wherein the overlap between the normalized emission spectrum of D and the normalized emission spectrum of A is 75% or less.

Aspect 49. The compound of Aspect 1, wherein the overlap between the normalized emission spectrum of D and the normalized emission spectrum of A is 25% or less.

Aspect 50. The compound of Aspect 1, the emission maximum of D is at least 25 nm from the emission maximum of A.

Aspect 51. The compound of Aspect 1, the emission maximum of D is at least 75 nm from the emission maximum of A.

Aspect 52. A method of detecting Cu(I) in a living cell, the method comprising:
   a) contacting the cell with a compound according to any one of aspects 1-51; and
   b) detecting ratiometric emission from the probe.

Aspect 53. The method of aspect 52, wherein the cell is in vitro.

Aspect 54. The method of aspect 52, wherein the cell is in vivo.

Aspect 55. The method of aspect 52, wherein the cell is a diseased cell.

Aspect 56. The method of any one of aspects 52-55, wherein the cell is a mammalian cell.

Aspect 57. The method of any one of aspects 52-56, wherein the cell is a neuron.

Aspect 58. The method of any one of aspects 52-57, comprising:
   a) measuring ratiometric emission from the probe at a first time; and
   b) measuring ratiometric emission from the probe at at least a second time that is later than the first time.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.
General Procedures Materials and Reagents. Fluorescein, phosphorous tribromide, 2-(aminomethyl)pyridine and thiophenol were purchased from Sigma-Aldrich. 6-(Bromomethyl)-2-pyridinemethanol and 2,6-bis(chloromethyl)pyridine were purchased from TCI America. 2-(4-Diethylamino-2-hydroxybenzoyl)benzoic acid was purchased from AK Scientific. 3-(1-Piperazinyl)phenol was purchased from Alfa Aesar. For the materials and reagents for in vitro and biological assays, copper(II) chloride and bathocuproine disulfonate (BCS) were purchased from Sigma-Aldrich. Dulbecco's modified Eagle's medium (DMEM; high glucose and no phenol red), GlutaMAX, fetal bovine serum (FBS) and phosphate-buffered saline (PBS) were purchased from Thermo Fisher Scientific. Fluorescein methyl ester (1), 4-nitro-N-(2-pyridinylmethyl)-benzenesulfonamide (2) and N-[9-(2-carboxyphenyl)-6-(1-piperazinyl)-3H-xanthen-3-ylidene]-N-ethyl-ethanaminium (3) were synthesized according to literature methods. All other reagents were of analytical grade and were used without further purification MilliQ water was used in all experiments unless otherwise stated.

Physical Measurements and Instrumentation. $^1$H NMR and $^{13}$C{$^1$H} spectra were collected at 25° C. on Bruker AVB-400, AVQ-400 and AV-300. All chemical shifts are reported in the standard δ notation of parts per million relative to residual solvent peak as an internal reference. Splitting patterns are indicated as follows: br, broad; s, singlet; d, doublet; t, triplet; m, multiplet; dd, doublet of doublets. Low-resolution electrospray mass spectra were recorded on a LC-MS (Agilent Technology 6130, Quadrupole LC/MS). High-resolution mass spectra were collected at the College of Chemistry Mass Spectrometry Facility. FCP-1 was characterized by LC-MS (Agilent Technology 6130, Quadrupole LC/MS) coupled with photodiode array for detection (λ=488 nm). UV-vis absorption spectra were recorded using a Varian Cary 50 spectrophotometer, and fluorescence spectra were recorded using a Photon Technology International Quanta Master 4 L-format scan spectrofluorometer equipped with an LPS-220B 75-W Xenon lamp and power supply, A-1010B lamp housing with integrated igniter, switchable 814 photocounting/analog photomultiplier detection unit, and MD5020 motor driver. Confocal microscopy images were recorded on a Zeiss laser scanning microscope 710 with a 20× or 63× oil-immersion objective lens using Zen 2009 software (Carl Zeiss). ICP-MS were recorded on a Thermo Fisher iCAP-Qc ICP-MS in Kinetic Energy Discrimination (KED) mode with the He flow set to 4.426 mL/min Measurements were normalized to a standard curve of known copper concentrations doped with 20 ppb Ga. The standard curve was diluted from CMS-5 (Inorganic Ventures).

Cell culture. Following cell cultures were grown: Human embryonic kidney (HEK 293T) cells were maintained in Dulbecco's Modified Eagle Medium (DMEM) supplemented with 10 vol % fetal bovine serum (FBS), 1 vol % GlutaMax (Gibco) and 1 vol % non-essential amino acids (NEAA, Gibco). Ctrl1$^{+/+}$ and Ctrl1$^{-/-}$ MEF cells were maintained in DMEM with 10 vol % FBS, 1 vol % non-essential amino acids, 1 vol % sodium pyruvate and 0.1 vol % 2-mercaptoethanol or DMEM supplemented with 10 vol % FBS and 1× Penicillin-Streptomycin. Human cervical epithelial carcinoma (HeLa) was maintained in DMEM medium supplemented with 1 vol % GlutaMAX and 10 vol % FBS. All cells were incubated in 5% $CO_2$ humidified air and subcultured at 80% confluence.

For MEFs (immortalized with a plasmid encoding the SV40-T-Ag gene), they were maintained in Dulbecco's Modified Eagle Medium (DMEM) supplemented with 10 vol % fetal bovine serum (FBS), 1× Penicillin/Streptomycin (PS) as described previously Immortalized MEFs were stably infected with retroviruses derived from pBABE (see plasmids below) or lentiviruses derived from pLKO.1 (see plasmids below) using established protocols. MEFs stably expressing non-targeting shRNA (Scr), Gclc shRNA, Gsr shRNA, KRAS$^{G12D}$ cDNA, or BRAF$^{V600E}$ cDNA were maintained in DMEM supplemented with 10 vol % FBS), 1×PS, and 2 μg/mL puromycin.

RNA extraction and Reverse transcriptase quantitative PCR. For RT-qPCR, RNA was purified from MEFs and reverse transcribed to cDNA using standard protocols and then quantified utilizing Taqman probes: Mm00558247_m1 to detect mouse Ctr1, Mm00437663_m1 to detect mouse Atp7a, Mm00439154_m1 to detect mouse Gsr, Mm00802655_m1 to detect mouse Gclc, Mm_01277042_m1 to detect mouse TATA binding protein (Tbp), Mm01318743_m1 to detect mouse Hprt and Mm02619580_g1 to detect mouse beta Actin (Actb) using the ViiA 7 Real-Time PCR System. Relative mRNA expression levels were normalized to Tbp, Actb, Hprt and analyzed using comparative delta-delta CT method and represented as a fold change.

Immunoblot analysis. Indicated cell lines were washed with cold PBS and lysed with cold RIPA buffer containing 1×EDTA-free Halt™ protease and phosphatase inhibitor cocktail halt protease and phosphatase inhibitors (Thermo Scientific). The protein concentration was determined by BCA Protein Assay (Pierce) using BSA as a standard. Equal amount of lysates were resolved by SDS-PAGE using standard techniques, and protein was detected with the following primary antibodies: mouse anti-γ-GCSc (1:1000, sc-390811, Santa Cruz Biotechnology), rabbit anti-glutathione reductase (1:1000, ab16801, Abcam), mouse anti-β-Actin (1:10000, 3700S, Cell Signaling), or rabbit anti-CCS (1:1000, sc-20141, Santa Cruz Biotechnology) followed by detection with one of the horseradish peroxidase conjugated secondary antibodies: goat anti-rabbit IgG (1:5000, 7074, Cell Signaling) or goat anti-mouse IgG (1:5000, 7076, Cell Signaling), using SignalFire (Cell Signaling) or SignalFire Elite ECL (Cell Signaling) detection reagents. The fold change in the total protein to actin was measured in Image Studio Lite (LI-CORE Biosciences) software by boxing each band per representative image using the rectangular selection tool and calculating the total signal of the band in pixels. The ratio of total protein to actin pixel intensity for each experimental condition was normalized to control and graphed as average fold change.

Total glutathione levels and reduced/oxidized glutathione ratios. MEFs were seeded at 20,000 cells/well in 96-well, white walled, flat clear bottom plates. Twenty-four hours after seeding, MEFs were treated with vehicle, 1 mM BSO or 0.1 mM BCNU for 4 hours and then assayed for totally glutathione levels or GSH/GSSG ratios. Total glutathione levels and the GSH/GSSG ratios were measured using the GSH/GSSG-Glo™ Assay kit from Promega (V6611) following the manufacturer's protocol for adherent cells. Total glutathione measurements and GSH/GSSG ratios were measured in four independent experiments assayed in triplicate. Statistical analysis of total glutathione and GSH/GSSG ratio was analyzed using a one-way ANOVA followed by a Dunnett's multi-comparisons test in Prism7 (GraphPad).

Confocal fluorescence microscopy imaging. For confocal fluorescence imaging experiments of HEK293T, MEF Ctr1$^{+/+}$ and Ctr1$^{-/-}$ and HeLa cells, the cells were plated on 8-well Lab Tek borosilicate chambered coverglass slides (Nunc), and allowed to grow to ca. 60% confluency before performing the cell imaging experiments. The confocal imaging was performed with a Zeiss laser scanning microscope 710 with 20× or 63× oil-immersion objective lens using Zen 2009 software (Carl Zeiss). FCP-1 was excited with 458 nm with an Ar laser, and the emissions were collected using a META detector between 465 and 541 nm ($F_{green}$), and between 559 and 710 nm ($F_{orange}$). DRAQ-5 was excited with a 633 nm He Ne laser, and its emission was collected using a META detector between 661 and 759 nm. Image analysis was performed using ImageJ, with ratiometric images generated by the Ratio Plus plugin of ImageJ. For quantification, a threshold value was set as background and the average intensity of the whole image was measured by ImageJ. All experiments were performed in triplicate, and statistical analyses were performed with a two-tailed Student's t-test (MS excel).

Example 1

Design, Synthesis and Characterization of FCP-1 and FL-TPA

FCP-1 was synthesized according to the method shown in FIG. 1. In particular, a fluorescein FRET donor and rhodamine FRET acceptor were linked through a copper-responsive TPA linker.

Figure 2:
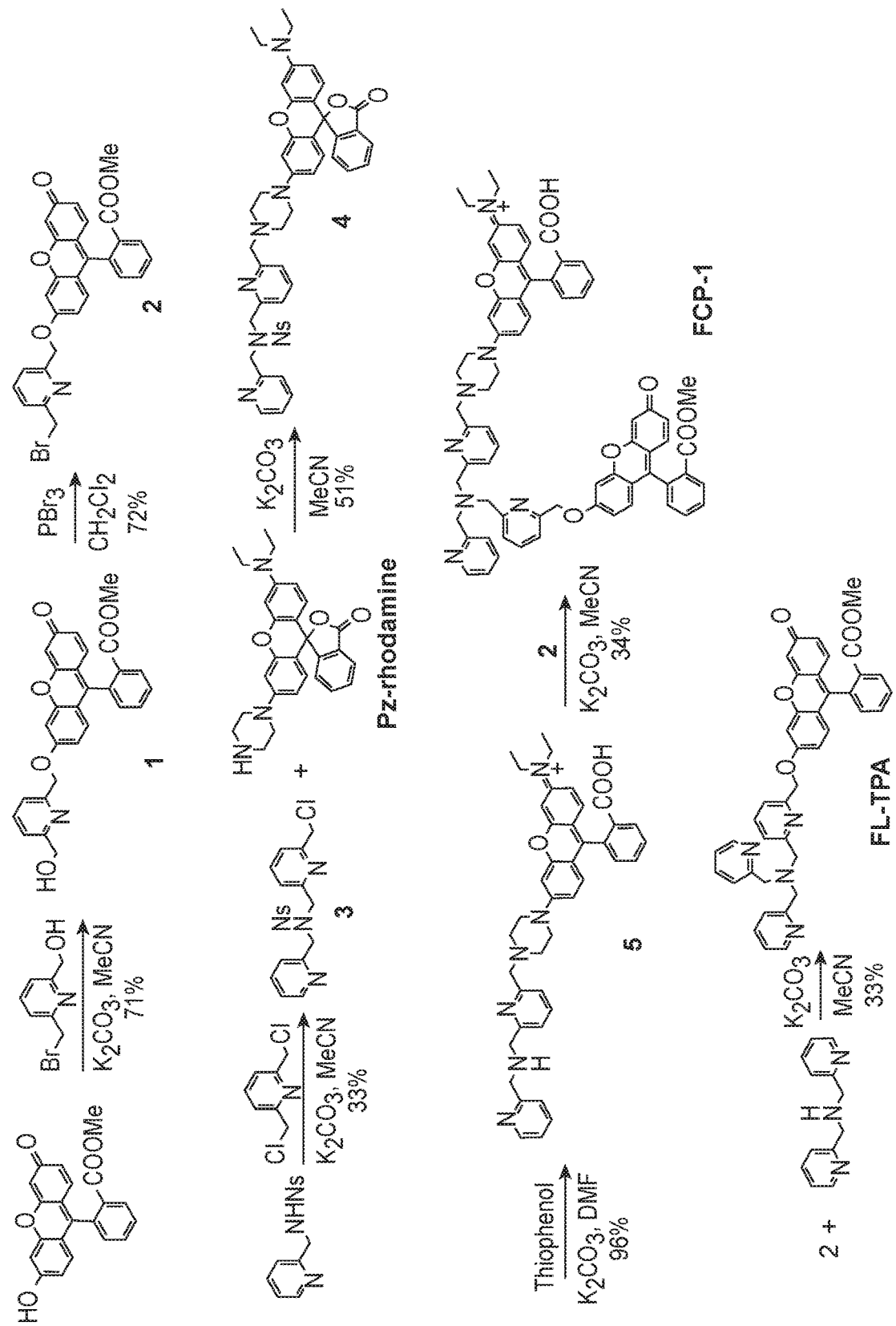
FIG. 2 shows the synthetic route to FCP-1 and control probe FL-TPA.

FCP-1 was synthesized according to the synthetic route shown in FIG. 2.

Figure 3:
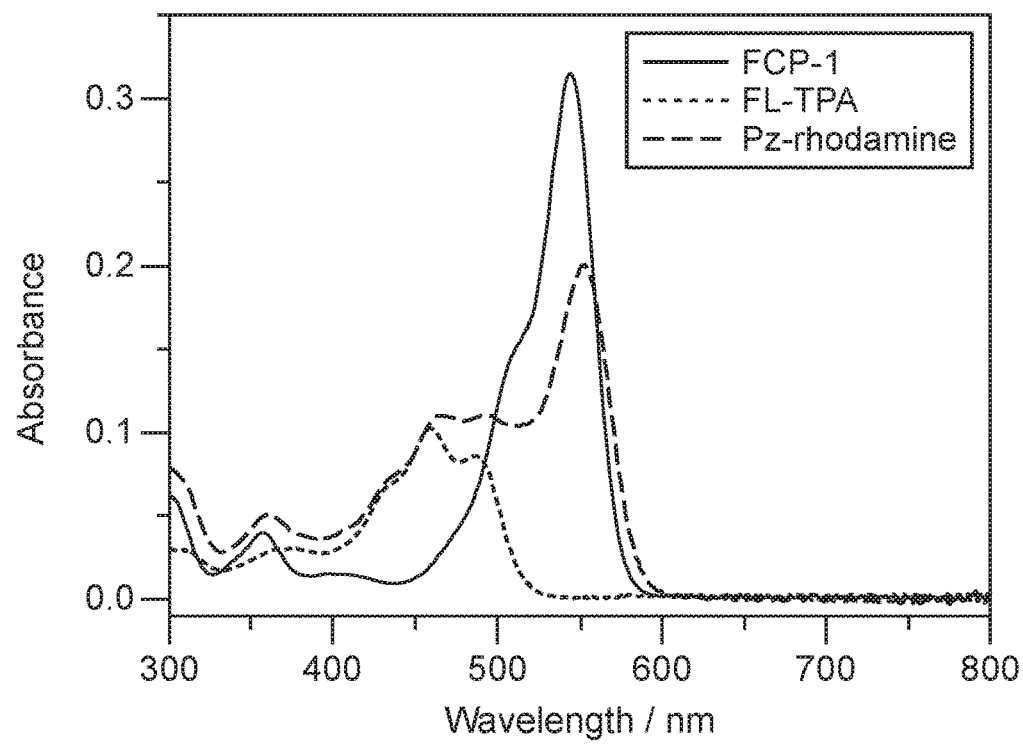
FIG. 3 shows a liquid chromatography trace of FCP-1 monitored at 488 nm.

The synthesis of FCP-1 starts with preparation of the 2-bromomethylpyridine-functionalized fluorescein methyl ester (2) and picolylamine-functionalized rhodamine (5; FIG. 2). Compound 2 was synthesized in 2 steps from the previously reported fluorescein methyl ester by nucleophilic substitution onto 6-(bromomethyl)-2-pyridinemethanol and subsequent bromination of the methyl alcohol. In parallel, nosyl-protected picolylamine (3) was prepared by monosubstitution of bis(chloromethyl)pyridine from 4-nitro-N-(2-pyridinylmethyl)benzenesulfonamide and then reacted with piperazinyl-functionalized rhodamine (Pz-rhodamine) to afford 4. Subsequently nosyl group of 4 is deprotected by thiophenol and $K_2CO_3$ to yield 5. With the key pieces 2 and 5 in hand, TPA motif can be generated through nucleophilic substitution of 2-bromomethyl group on 2 by the picolylamine on 5 under basic conditions, furnishing the final ratiometric probe FCP-1 that was characterized by $^1H$ and $^{13}C\{^1H\}$ NMR, high-resolution mass spectrometry (HRMS), and liquid chromatography-coupled mass spectrometry (LCMS; FIG. 3). The intensity-based Cu(I) probe FL-TPA was prepared as a control compound with the same Cu(I)-dependent activity-based sensing trigger and fluorescein scaffold but lacking a ratiometric response (Scheme 2).

2-[3-(2-Hydroxymethyl-6-pyridylmethoxy)-6-hydroxyl-9H-xanthen-9-yl]benzoic acid methyl ester (1). Fluorescein methyl ester (44.2 mg, 0.13 mmol) and 6-(Bromomethyl)-2-pyridinemethanol (28.4 mg, 0.14 mmol) were dissolved in dry acetonitrile (30 mL). Potassium carbonate (97.0 mg, 0.70 mmol) was added to the solution, and the reaction mixture was heated at 85° C. overnight. The solution mixture was cooled to room temperature, and any undissolved solid was filtered off. The filtrate was evaporated under reduced pressure, and the product was purified by column chromatography on silica gel using ethyl acetate-methanol (25:1, v/v) as the eluent, yielding the desired product as an orange-yellow solid (42.5 mg, 71%).

2-[3-(2-Bromomethyl-6-pyridylmethoxy)-6-hydroxyl-9H-xanthen-9-yl]benzoic acid methyl ester (2). 1 (42.5 mg, 0.09 mmol) was dissolved in dry dichloromethane (30 mL), and phosphorous tribromide (5.12 μL, 0.5 mmol) in dry dichloromethane (10 mL) was added dropwise to the solution at 0° C. The reaction mixture was then allowed to warm up to room temperature and stir for 3 h. The reaction was quenched by sat. NaHCO₃(aq) solution, and the aqueous layer was extracted with dichloromethane three times. The volatile organic solvent was evaporated under reduced pressure, and the product was purified by column chromatography on silica gel using ethyl acetate as the eluent, yielding the desired product as an orange-yellow solid (34.8 mg, 72%).

N-[(6-Chloromethyl-2-pyridinyl)nethyl]-4-nitro-N-(2-pyridinylmethyl)-benzenesulfonamide (3). 4-nitro-N-(2-pyridinylmethyl)-benzenesulfonamide (300 mg, 1.02 mmol) and 2,6-bis(chloromethyl)pyridine (180.1 mg, 1.02 mmol) were dissolved in dry acetonitrile (30 mL). Potassium carbonate (212.1 mg, 1.53 mmol) was added to the solution, and the reaction mixture was heated at 85° C. overnight. The solution mixture was cooled to room temperature, and any undissolved solid was filtered off. The filtrate was evaporated under reduced pressure, and the product was purified by column chromatography on silica gel using hexane-ethyl acetate (1:1, v/v) as eluent, yielding the desired product as a pale yellow oil (146.9 mg, 33%).

Compound 4. N-[9-(2-carboxyphenyl)-6-(1-piperazinyl)-3H-xanthen-3-ylidene]-N-ethyl-ethanaminium (188.7 mg, 0.41 mmol) and 3 (196.8 mg, 0.45 mmol) were dissolved in dry acetonitrile (30 mL). Potassium carbonate (212.1 mg, 1.53 mmol) was added to the solution, and the reaction mixture was heated at 85° C. overnight. The solution mixture was cooled to room temperature, and any undissolved solid was filtered off. The filtrate was evaporated under reduced pressure, and the product was purified by column chromatography on alumina using ethyl acetate-methanol (9:1, v/v) as eluent, yielding the desired product as pale pink film (180.1 mg, 51%).

Compound 5. 4 (42.6 mg, 0.05 mmol) was dissolved in dry dimethylformamide (2 mL). Potassium carbonate (31.7 mg, 0.23 mmol) was added to the solution, followed by the addition of thiophenol (51.3 μL, 0.43 mmol). The solution mixture was stirred at room temperature overnight. The solvent was evaporated under vacuum, and the crude product was re-dissolved in ethyl acetate. Any undissolved solid was filtered off, and the organic solvent was evaporated under reduced pressure. The crude product was dissolved in minimum amount of dichloromethane with 1 vol % trifluoroacetic acid, and precipitated by adding large volume of diethyl ether. The solid was further washed by diethyl ether twice, and dried under vacuum to yield the desired product as purple film (37.5 mg, 96%).

FCP-1. Compounds 2 (11.0 mg, 0.021 mmol) and 5 (20.2 mg, 0.021 mmol) were dissolved in dry acetonitrile (30 mL). Potassium carbonate (20.1 mg, 0.145 mmol) was added to the solution, and the reaction mixture was heated at 85° C. overnight. The solution mixture was cooled to room temperature, and any undissolved solid was filtered off. The filtrate was evaporated under reduced pressure, and the product was purified by prep-HPLC. The mobile phase was a mixture of 0.1% formic acid in water (phase A) and 0.1% formic acid in methanol (phase B). Separation was achieved by using: 50% phase B at t=0 min; 50-100% phase B from 0 to 40 min; 100% phase B from 40 to 100 min. The flow rate was 1.5 mL/min and the injection volume was 2 mL. The solvent mixture was evaporated under vacuum, yielding the desired product as red film (7.8 mg, 34%).

FL-TPA. Compound 2 (40 mg, 0.075 mmol) and di-(2-picolyl)amine (15.0 mg, 0.075 mmol) were dissolved in dry acetonitrile (30 mL). Potassium carbonate (57.3 mg, 0.41 mmol) was added to the solution, and the reaction mixture was heated at 85° C. overnight. The solution mixture was cooled to room temperature, and any undissolved solid was filtered off. The filtrate was evaporated under reduced pressure, and the product was purified by column chromatography on alumina using ethyl acetate-methanol (49:1, v/v) as eluent, yielding the desired product as yellow-orange film (15.0 mg, 31%).

LC-MS characterization of FCP-1. FCP-1 were dissolved in a H₂O/MeOH solution mixture, and an aliquot was taken for LC-MS analysis. Separation was achieved by gradient elution from 5-100% MeOH in water (constant 0.1 vol % formic acid) over 8 min, isocratic with 100% MeOH from 8 to 12 min and returned to initial conditions and equilibrated for 3 minutes. The LC chromatograms were recorded by monitoring absorption at 488 nm.

UV-vis absorption and emission measurements. FCP-1 stock solution in DMSO (5 mM) was prepared, aliquoted and stored at 20° C. For each spectroscopic measurement, a fresh aliquot was diluted to 500 μM by DMSO and further diluted with PBS containing 2 mM GSH/PEG-400 mixture (3:2, v/v) to prepare the sensing solution with 5 μM of FCP-1. The sensing solution was pre-incubated in a water bath at 37° C., and then [Cu(CH₃CN)](PF₆) in MeCN or other metal ions in H₂O was added. The solution mixture was kept at 37° C. and taken out for UV-vis absorption or emission spectroscopic measurements in quartz cuvette at predetermined time intervals. Emission spectra were corrected using coumarin 153 as secondary emission standard (4). Photoluminescence quantum yield (PLQY) was determined using fluorescein in 0.1 M NaOH solution (0.95; $\lambda_{ex}$=496 nm). FRET efficiency from the fluorescein moiety to rhodamine moiety of FCP-1 was estimated by [1−(PLQY of FCP-1/PLQY of FL-TPA)].

Inductively coupled plasma-mass spectrometry (ICP-MS). HeLa cells were plated on 6-well plates. At ca. 40% confluency, the cells were treated with solvent control, different concentrations of CuCl₂ or BCS (100 μM) in complete medium for 24 h. The cells were then washed with 20 mM HEPES buffer (pH 7.4) three times and then digested in concentrated nitric acid (100 mg/mL HNO₃, BDH Aristar Ultra) overnight and heated up at 90° C. for 2 h in 1.5 mL tubes (Sarstedt) with small holes poked in the caps. Once cooled to room temperature, samples were diluted into 2% HNO₃ and doped with a gallium internal standard (Inorganic Ventures, 20 ppb final concentration). The copper and phosphorous content was determined by measuring $^{63}$Cu and $^{31}$P using a Thermo Fisher iCAP-Qc ICP-MS in Kinetic Energy Discrimination (KED) mode with the He flow set to 4.426 mL/min. Measurements were normalized to a standard curve of known copper concentrations doped with 20 ppb Ga. The standard curve was diluted from CMS-5 (Inorganic Ventures).

Similarly, mouse embryonic fibroblasts (MEF) Ctrl$^{+/+}$ and Ctrl$^{-/-}$ cells were grown on 6-well plates. At ca. 70% confluency, the cells were washed with PBS three times, digested in concentrated nitric acid overnight, heated up at 90° C. for 2 h and then diluted into 2% HNO₃ and doped with a gallium internal standard. The solutions were then assayed for copper and phosphorous content by measuring $^{63}$Cu and $^{31}$P using a Thermo Fisher iCAP-Qc ICP-MS.

Example 2

Reactivity and Selectivity of FCP-1 to Copper

Figure 4:
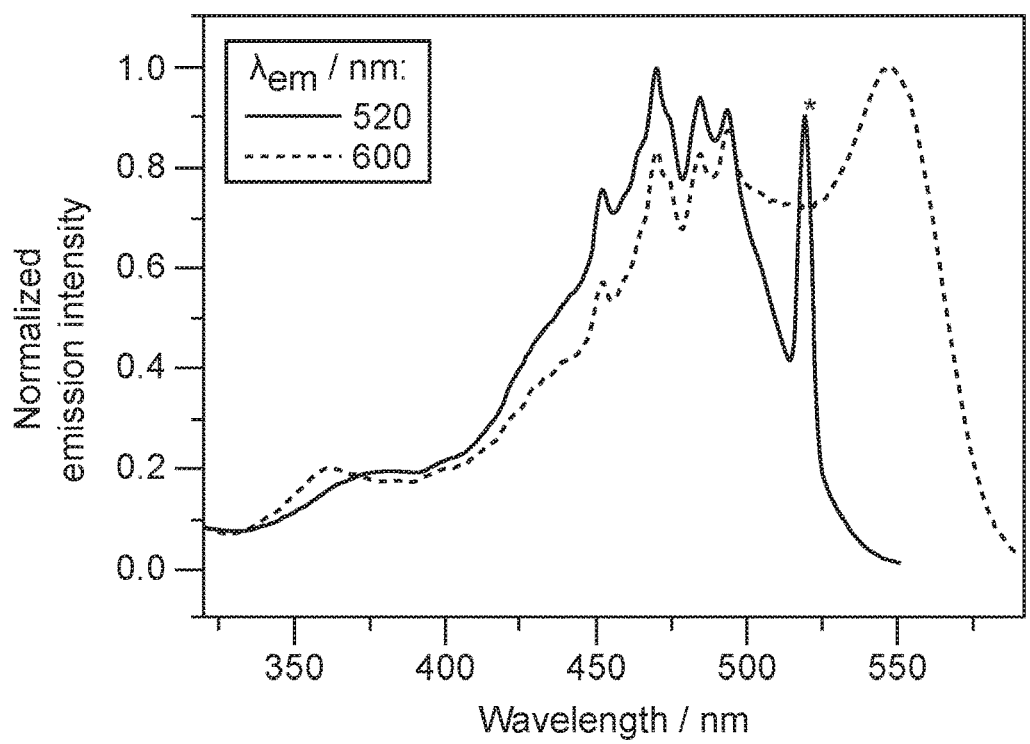
FIG. 4 shows the UV-vis absorption spectra of FCP-1, FL-TPA and Pz-rhodamine (5 μM) in PBS containing 2 mM GSH with 40 vol % PEG-400.
Figure 6:
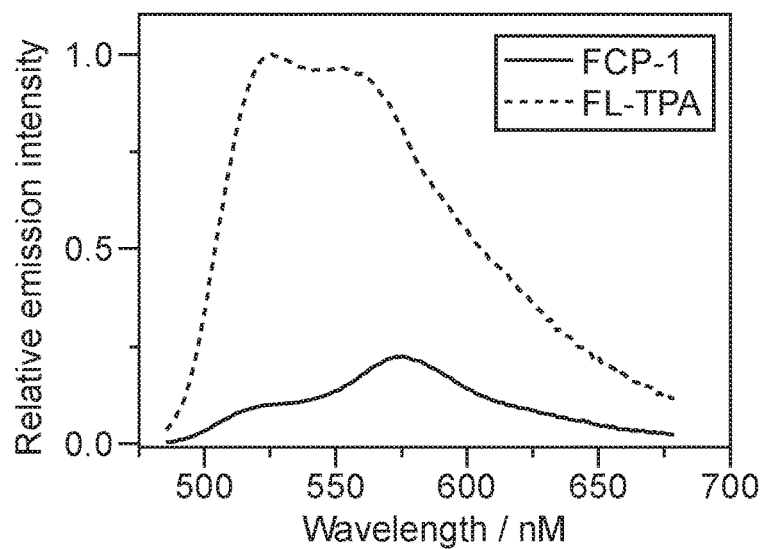
FIG. 6 shows the normalized excitation spectra of FCP-1 (5 μM) in PBS containing 2 mM of GSH with 40 vol % PEG-400. Asterisk denotes scattering from the fluorescence of FCP-1.
Figure 7:
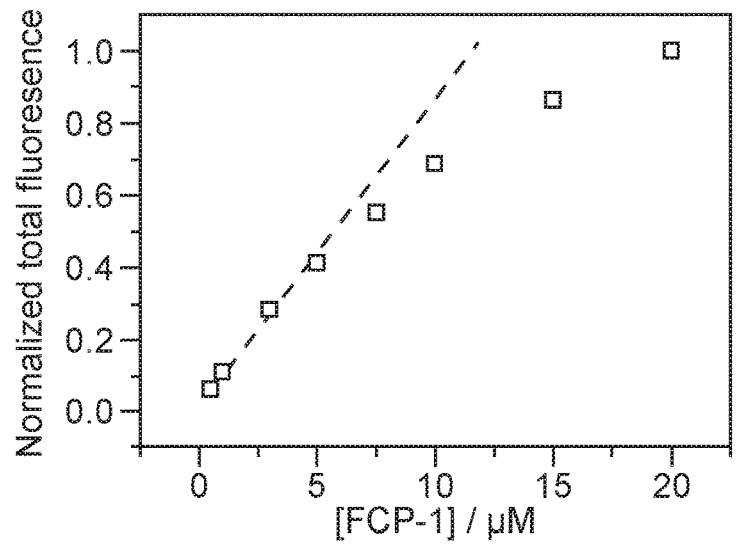
FIG. 7 shows the corrected emission spectra of FCP-1 (5 μM) and FL-TPA (5 μM) in PBS containing 2 mM GSH with 40 vol % PEG-400. $\lambda_{ex}$=458 nm.

FCP-1 in PBS buffer containing glutathione (2 mM) and PEG-400 (40%, v/v) was evaluated. FCP-1 showed absorption maxima at 465, 493 and 552 nm, with molar extinction coefficients of 20,000, 22,100 and 40,000 M$^{-1}$ cm$^{-1}$, respectively (FIG. 4). The first two absorption maxima corresponded to the absorption of the fluorescein moiety, as similar absorption maxima at 460 and 489 nm were found in the absorption spectra of FL-TPA (FIG. 4), whereas the lowest energy absorption at 552 nm originated from the rhodamine moiety (FIG. 4). Upon photoexcitation at 458 nm, FCP-1 was found to emit at 526 and 576 nm (FIG. 5), corresponding to fluorescein and rhodamine signatures, respectively. Notably, the Pz-rhodamine building block shows only weak absorption at 458 nm (FIG. 4). Together with the significant contribution of the lower-energy fluorescence from the excitation at 450-500 nm, which is in the region of FL-TPA absorption (FIG. 6), the data support the occurrence of FRET from the fluorescein donor to the rhodamine acceptor. Using FL-TPA as a reference FRET donor compound (FIG. 7) with assumption that quenching of donor fluorescence originated only from the FRET process, the FRET efficiency in the FCP-1 cassette is estimated to be 84%.

Figure 8:
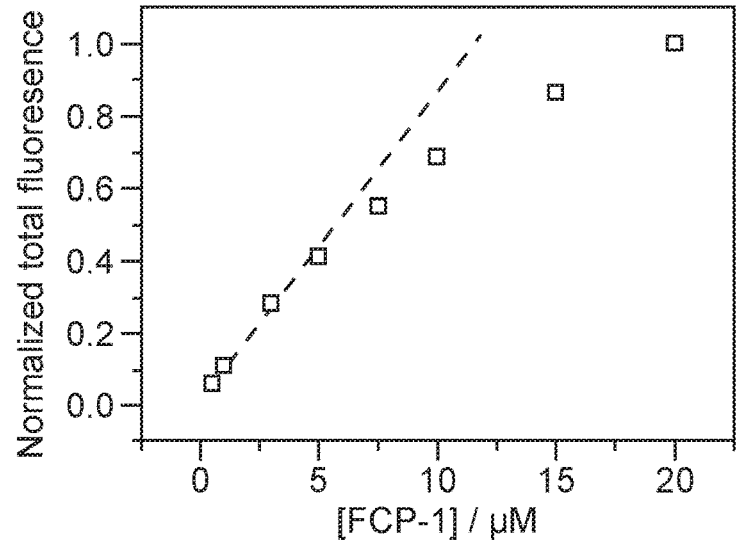
FIG. 8 shows changes in total fluorescence intensity of FCP-1 in aqueous buffer solution (PBS with 2 mM GSH and 40 vol % PEG-400) at different concentrations. $\lambda_{ex}$=458 nm.

Upon addition of Cu(I), FCP-1 showed an increase in fluorescein emission at 526 nm over time, with a concomitant drop in rhodamine fluorescence at 576 nm (FIG. 5, panel A), consistent with the Cu(I)-triggered oxidative cleavage of benzyl ether C—O bond on the TPA linker to separate the fluorescein donor and rhodamine acceptor moieties, leading to a decrease in intramolecular FRET efficiency. The ratiometric fluorescence change of FCP-1 at 526 and 576 nm ($F_{526}/F_{576}$) was rapid and reached saturation after ca. 30 min in the presence of a two-fold excess of Cu(I) (10 μM). Notably, the basal $F_{526}/F_{576}$ FCP-1 emission ratio did not show significant changes with varying concentrations of probe (0.5 to 20 μM, FIG. 5, panels B-C). This internal self-calibration is advantageous, as FCP-1 was found to be less fluorescent at higher concentrations, presumably due to self-quenching, which is a common issue found in fluorophores (FIG. 8) (62). Indeed, the negligible changes in ratiometric emission of FCP-1 indicated that FRET occurred primarily through an intramolecular mechanism, and concentration-independent ratiometric fluorescence of FCP-1 further highlights its potential in comparative imaging of labile Cu(I) pools in biological specimens by avoiding potential complications arising from variations in probe uptake, sample thickness, and light intensity.

Figure 5:
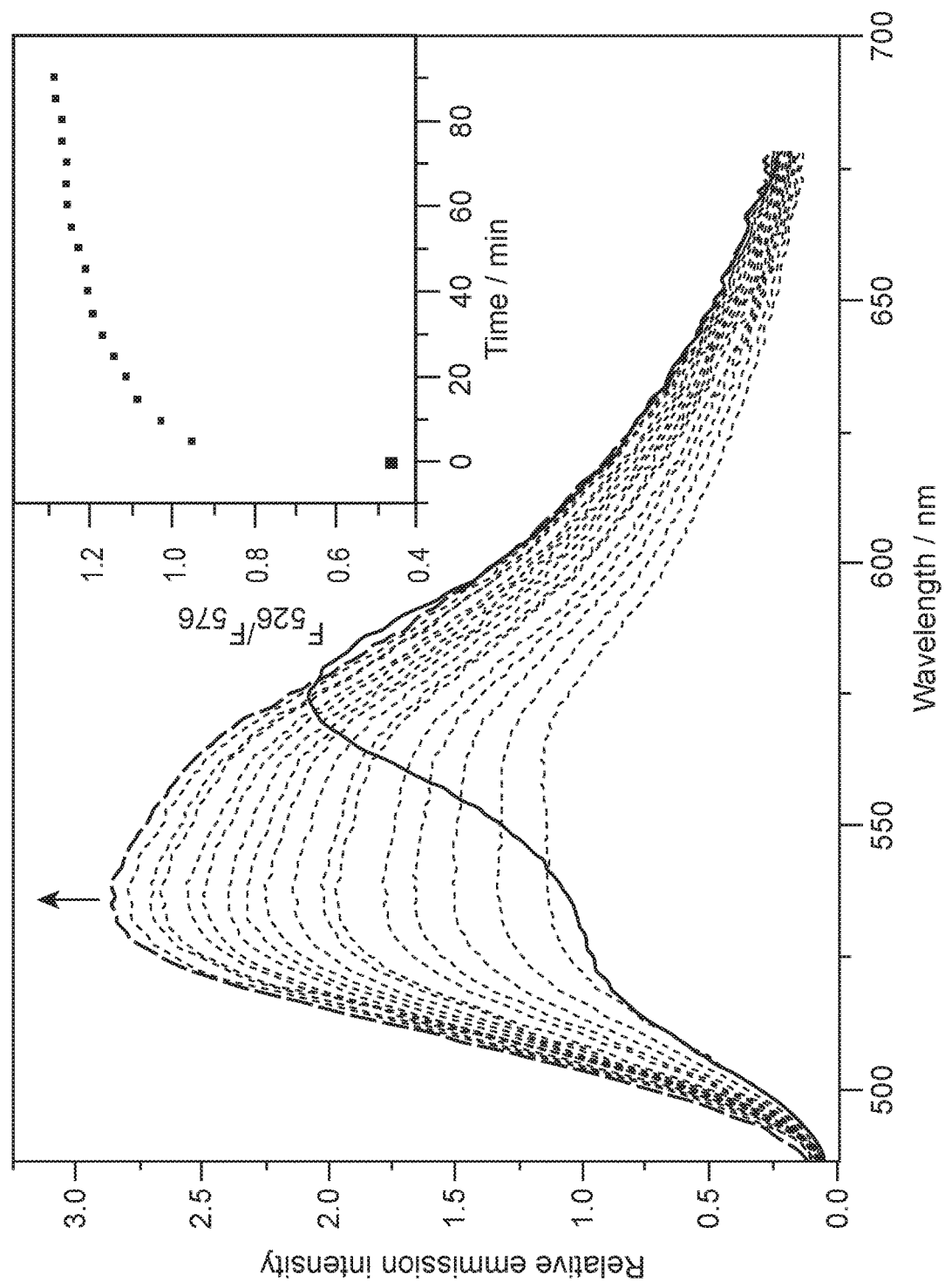
FIG. 5 shows the photophysical properties and Cu(I) selectivity of FCP-1 in aqueous buffer solutions. (A) Changes in corrected emission spectra of FCP-1 (5 μM) in aqueous buffer solution. Inset shows changes in ratiometric emission of FCP-1, $F_{526}/F_{576}$, with Cu(I) (10 μM) over time. (B) Corrected emission spectra of FCP-1 measured at various concentrations. (C) No significant changes in the $F_{526}/F_{576}$ emission ratio with varying concentrations of FCP-1 are observed. (D) Changes in $F_{526}/F_{576}$ ratio of FCP-1 (5 μM) towards various biologically relevant metal ions, as well as cobalt(II)-containing vitamin B12. Black bars represent the ratiometric emission response observed upon addition of competing metal ions (1 mM for $Na^+$, $K^+$, $Mg^{2+}$ and $Ca^{2+}$, and 10 μM for all the other d-block metal ions as well vitamin B12) after 15 min. Red bars represent the ratiometric emission response upon subsequent addition of 10 μM of Cu(I) after 15 min. (E) Emission spectra and (F) $F_{526}/F_{576}$ emission ratio of FCP-1 (5 μM) with addition of Cu(II) (10 μM), Cu(II) (10 μM)+GSH (2 mM), or Cu(I) (10 μM)+GSH (2 mM) after 15 min. All spectra were acquired in aqueous buffer (PBS with 2 mM GSH and 40 vol % PEG-400) with $\lambda_{ex}$=458 nm.
Figure 5:
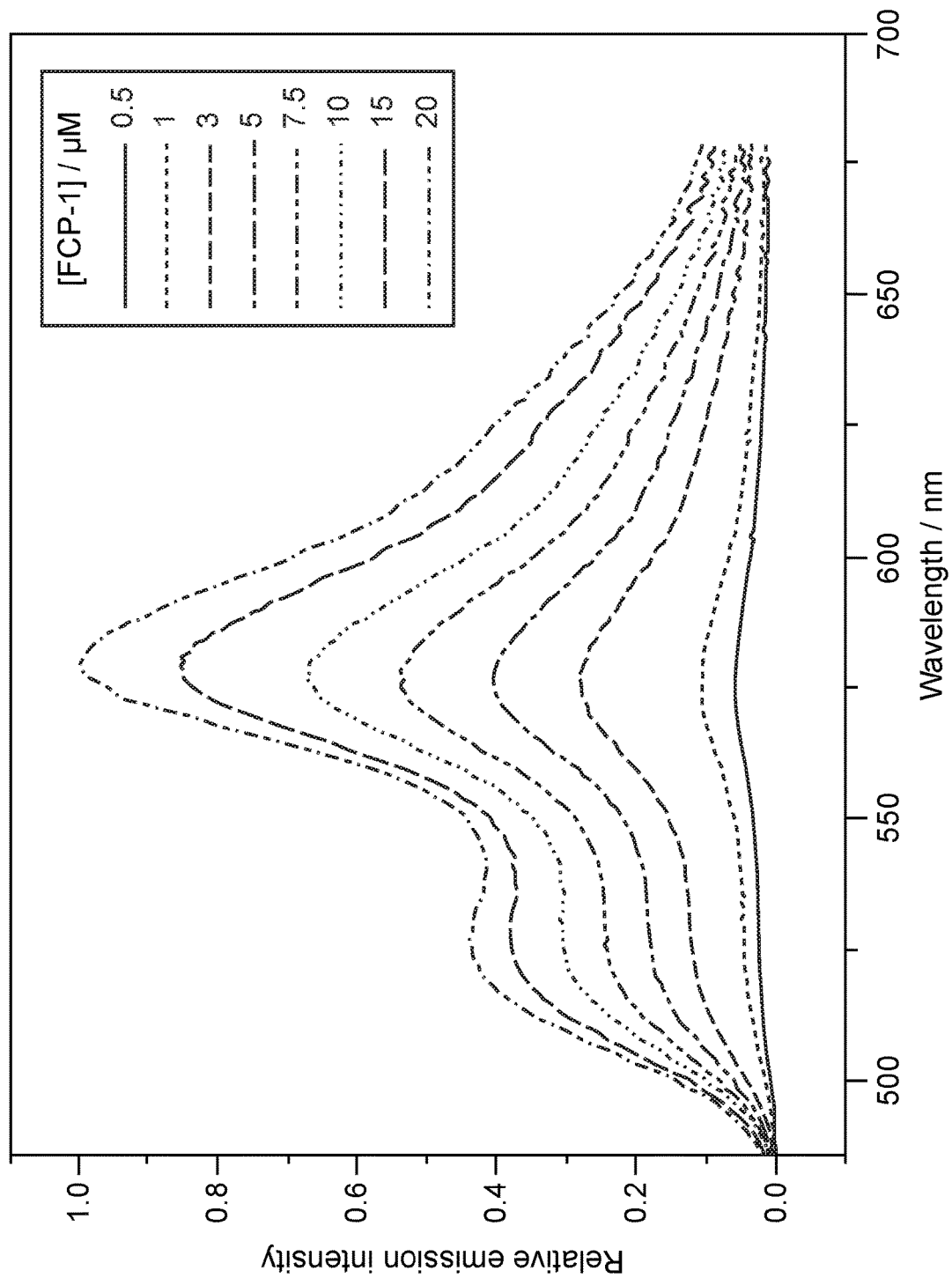
Figure 5:
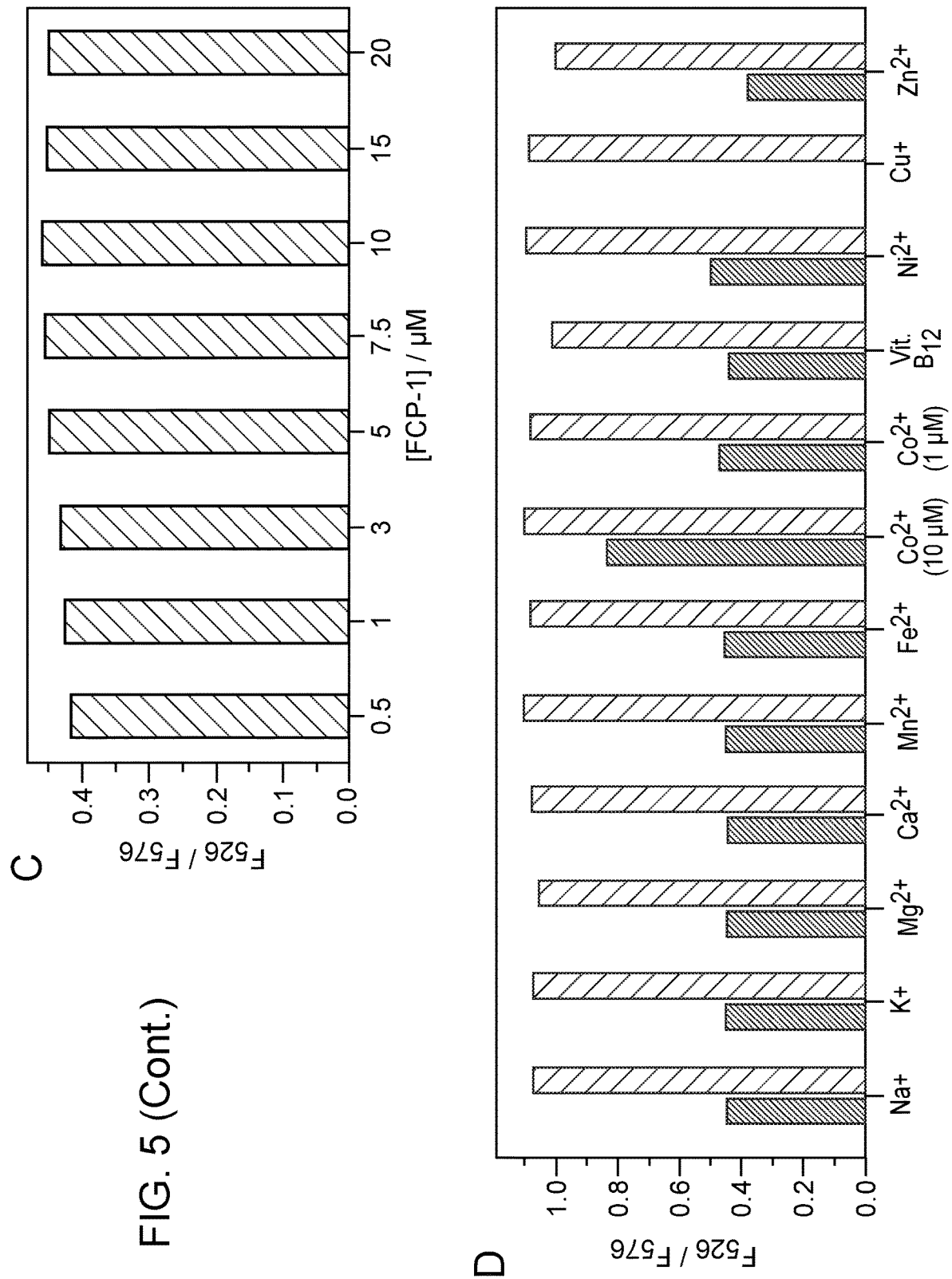
Figure 5:
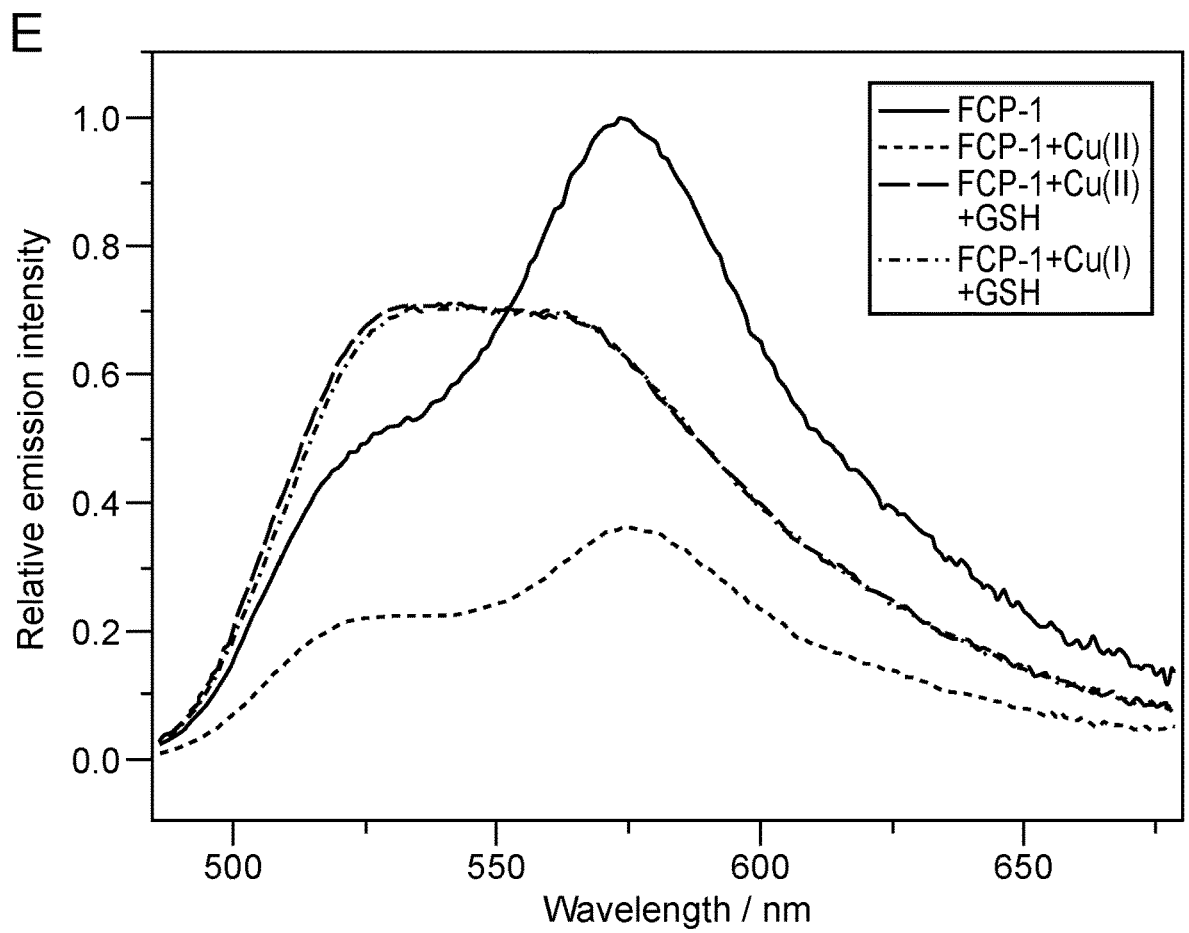
Figure 5:
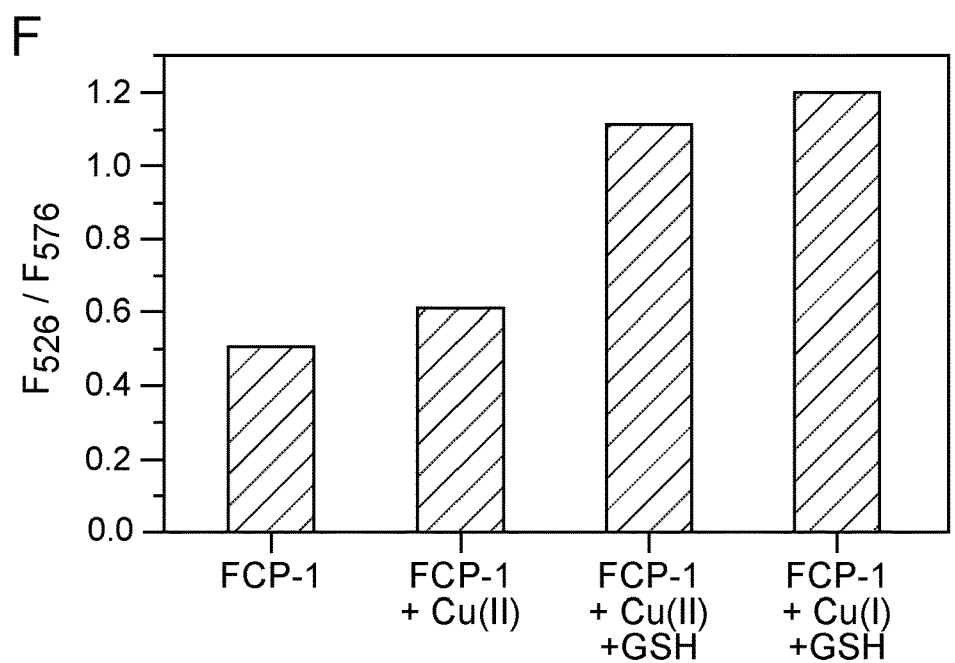

The ratiometric fluorescence change of FCP-1 was selective toward Cu(I) over other biologically relevant metal ions, except free Co(II) at 10 μM, which altered FCP-1 fluorescence modestly (FIG. 5, panel D). Notably, this concentration of exogenous Co(II) is far higher than the physiologically relevant levels of labile Co(II), as this metal ion is known to be tightly bound by proteins. Indeed, FCP-1 showed no significant changes in ratiometric signal in the presence of 10 μM cobalamin (vitamin $B_{12}$) (63), which is the predominant form of Co(II) in mammalian systems. Competitive experiments further showed the ability of FCP-1 to detect Cu(I) in solutions containing other biologically relevant metal ions (FIG. 5, panel D). In addition to exhibiting metal selectivity, the ratiometric response of FCP-1 is oxidation state-specific for Cu(I), as the probe does not respond ratiometrically to Cu(II) (FIG. 5, panels E-F). In further support of this oxidation state selectivity, co-incubation of FCP-1 with Cu(II) and excess glutathione, which readily reduces Cu(II) to Cu(I), resulted in emission spectra and a $F_{526}/F_{576}$ ratio that is identical to that obtained by treating FCP-1 with Cu(I) and excess glutathione (FIG. 5, panels E-F). This oxidation state-specificity is important for the applications of FCP-1 in imaging dynamic changes in intracellular labile Cu(I) pools under redox stress and oncogenic transformation.

Example 3

FCP-1 can Image Labile Cu(I) Pools in Living Cells

Figure 9:
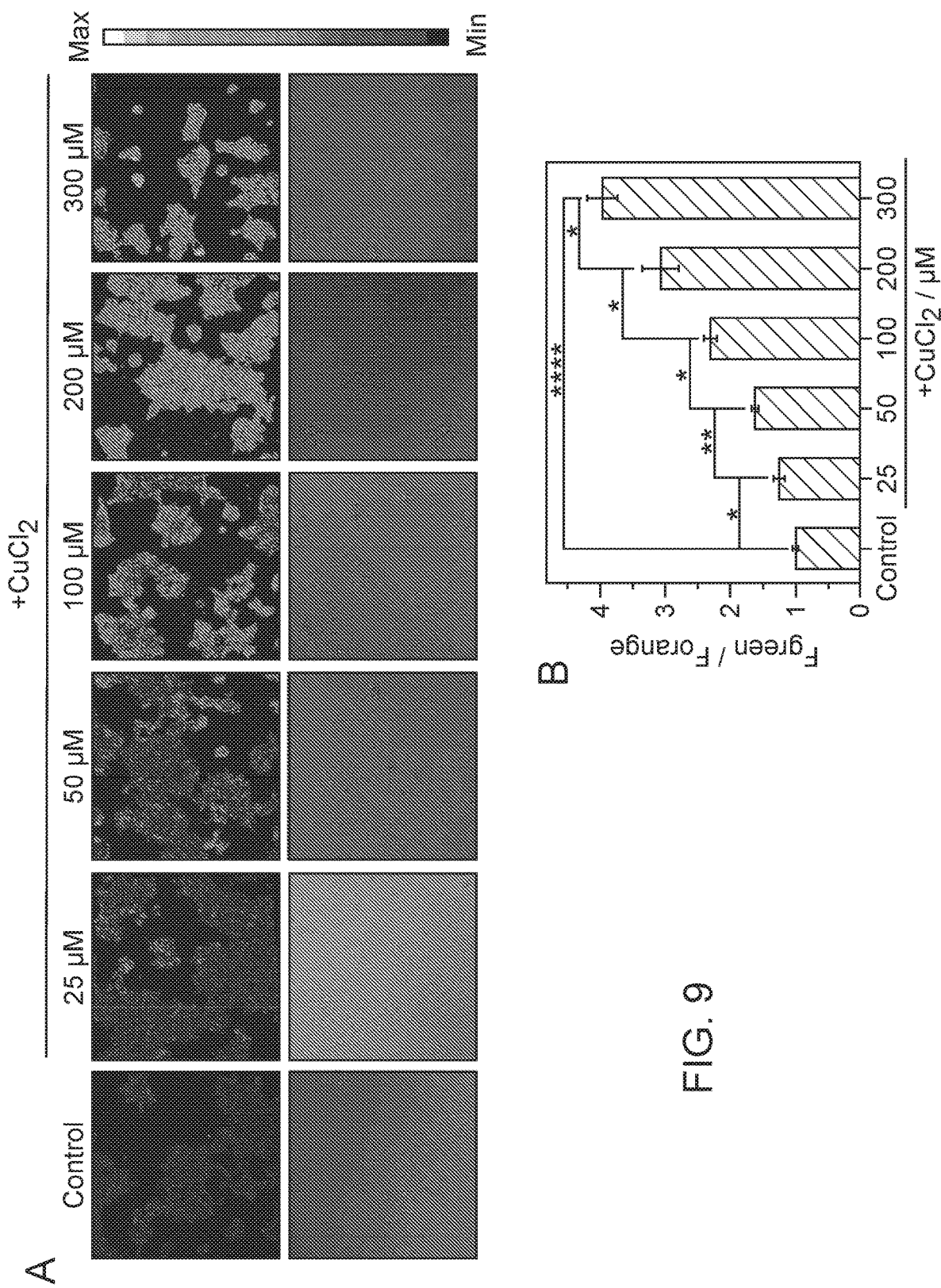
FIG. 9 shows Ratiometric fluorescence imaging of labile Cu(I) levels in living cells using FCP-1. (A) Confocal fluorescence microscopy images of HEK 293T cells pretreated with solvent vehicle control or varying concentrations of $CuCl_2$ in complete medium for 18 h. The cells were then washed with PBS, incubated with FCP-1 (5 μM) in DPBS for 45 min and then imaged. (B) Average cellular ratiometric emission ratios, represented by $F_{green}/F_{orange}$, as determined from imaging experiments in (A) performed in triplicate. (C) Confocal fluorescence microscopy images of HEK 293T cells pretreated with solvent vehicle control or BCS (100 μM) in complete medium for 18 h. The cells were then washed with PBS, incubated with FCP-1 (5 μM) in DPBS for 45 min and then imaged. (D) Average cellular ratiometric emission ratios of FCP-1, $F_{green}/F_{orange}$, as determined from experiments in (C) performed in triplicate. Panels (A) and (C) are displayed in pseudocolor and referenced to the basal control for that experiment and independently from each other. $\lambda_{ex}$=458 nm. (E) ICP-MS measurement to determine total cellular $^{63}Cu$ levels in HEK293T cells under copper supplementation and depletion relative to the control (with normalization of different cell numbers by total cellular $^{31}P$ level). Error bars denote standard derivation (SD; n=3). *p<0.05, p<0.01, *p<0.001, **p<0.0001 and ***p<0.00001.
Figure 9:
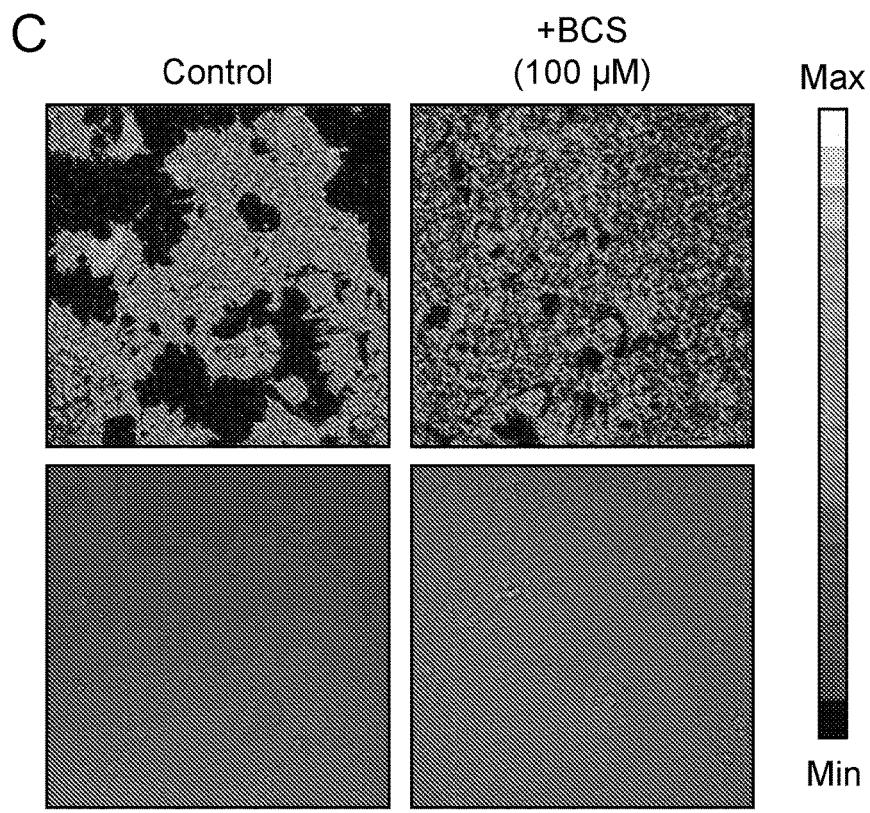
Figure 9:
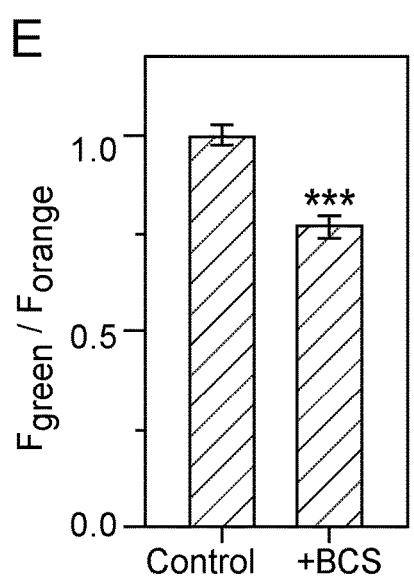
Figure 9:
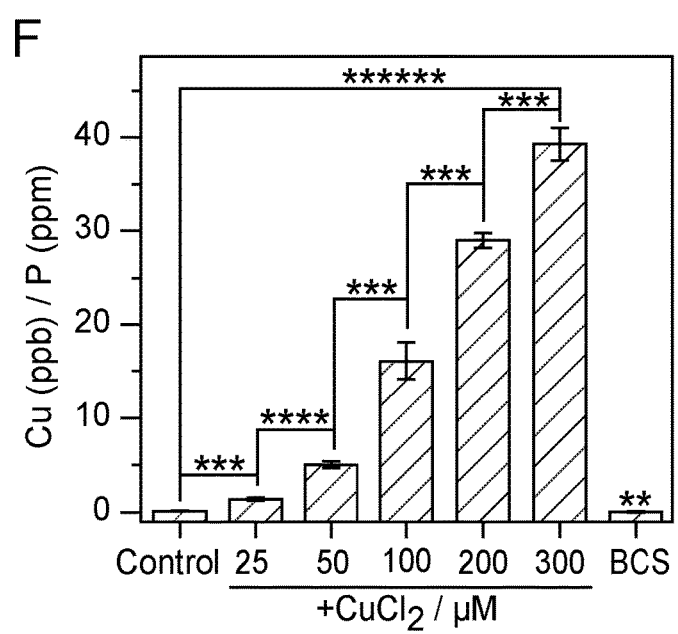
Figure 10:
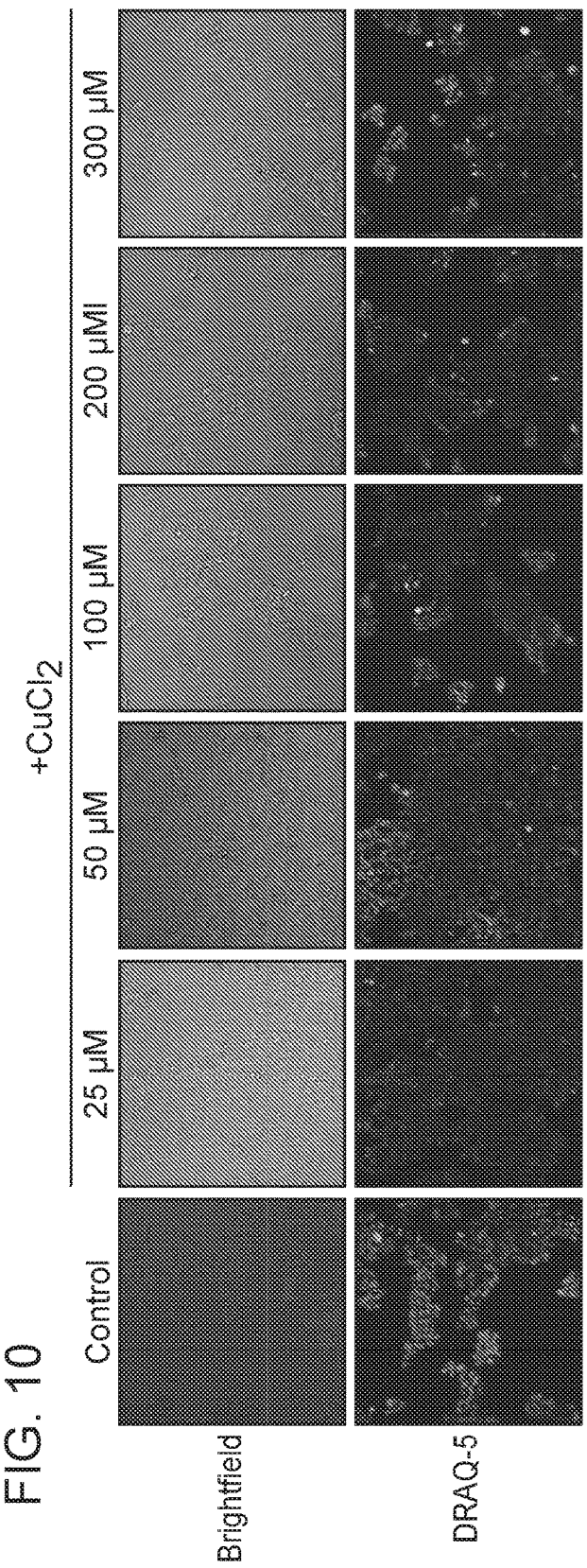
FIG. 10 shows confocal microscopy images of HEK 293T cells pretreated with solvent vehicle or different concentrations of CuCl2 in complete medium for 18 h, washed with PBS and stained with FCP-1 (5 μM) in DPBS for 45 min. At the last 5-min incubation, a nucleus stain, DRAQ-5 (5 μM), was added to the solution mixture. Without washing, the cells were imaged by confocal fluorescence microscopy.
Figure 11:
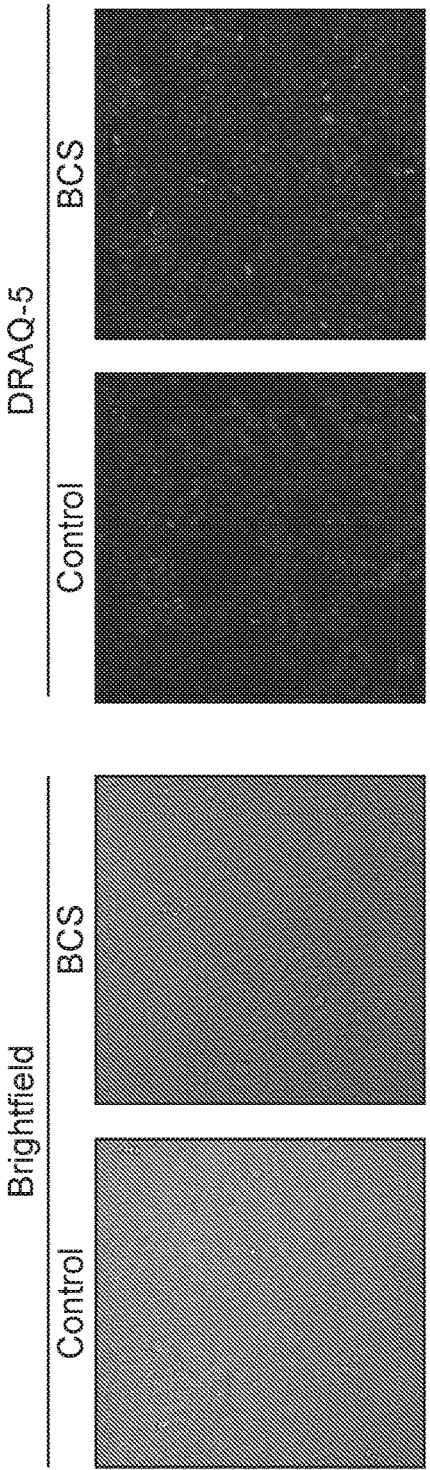
FIG. 11 shows confocal microscopy images of HEK 293T cells pretreated with solvent vehicle or BCS (100 μM) in complete medium for 18 h, washed with PBS and stained with FCP-1 (5 μM) in DPBS for 45 min. At the last 5-min incubation, a nucleus stain, DRAQ-5 (5 μM), was added to the solution mixture. Without washing, the cells were imaged by confocal fluorescence microscopy.

Given the metal and oxidation state-selective and sensitive response of FCP-1 to Cu(I), this probe was examined for ratiometric fluorescence imaging of labile Cu(I) pools in living cells. To this end, HEK 293T cells were exposed to varying doses of $CuCl_2$ (25-300 μM), washed thoroughly to remove excess copper from the medium, and then incubated with FCP-1 (5 μM) for 45 min and imaged. The copper-supplemented cells showed a statistically significant, dose-dependent increase in $F_{green}/F_{orange}$ ratio over vehicle control cells (FIG. 9, panel A). In contrast, copper-deficient HEK 293T cells obtained by treatment with a membrane-impermeable copper chelator, bathocuproine sulfonate (BCS; 100 μM), washed, and subsequently incubated with FCP-1 (5 μM) exhibited a statistically significant decrease in $F_{green}/F_{orange}$ ratio when compared to control cells (FIG. 9, panel B). The observed increases and decreases in labile Cu(I) levels upon copper supplementation ($CuCl_2$) and copper depletion (BCS) treatments, respectively, as measured by FCP-1 imaging were supported by complementary ICP-MS measurements of total copper levels showing expected increases and decreases in the total copper pool (FIG. 9, panel C). Control experiments showed that the cells remained viable as indicated by nuclear staining (FIGS. 10-11). These data establish that FCP-1 is capable of visualizing both increases and decreases in labile Cu(I) pools in living cells by a ratiometric fluorescence readout.

Example 4

FCP-1 can Monitor Differences in Labile Cu(I) Levels in a Genetic Cell Model of Copper Misregulation Having established that FCP-1 is sensitive to endogenous pools of labile Cu(I) under basal conditions and can respond to changes in labile Cu(I) pools upon pharmacological copper supplementation and/or depletion, the application of FCP-1 to visualize alterations in endogenous labile Cu(I) pools through genetic manipulation was explored. To this end, comparative FCP-1 imaging was performed in mouse embryonic fibroblast cells that are either Cu-replete ($Ctr1^{+/+}$ MEFs) or Cu-deficient ($Ctr1^{-/-}$ MEFs) through knockout of the high-affinity copper transporter CTR1 (64-66). As expected, $Ctr1^{+/+}$ MEFs incubated with FCP-1 exhibited higher $F_{green}/F_{orange}$ ratios as compared to the $Ctr1^{-/-}$ MEFs (p<0.01; FIGS. 12A-B), indicating that FCP-1 can precisely detect a relative decrease in endogenous levels of labile Cu(I) in cells deficient in copper uptake.

Figure 13:
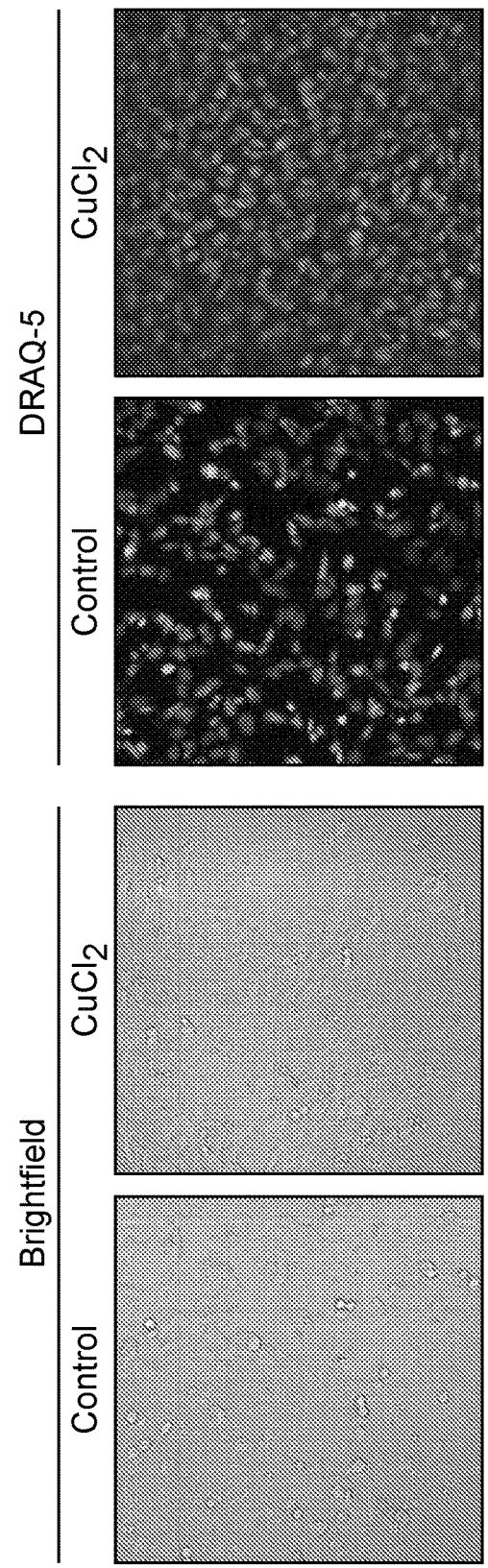
FIG. 13 shows confocal microscopy images of Ctrl$^{+/+}$ MEFs pretreated with solvent vehicle or CuCl$_2$ (300 µM) in complete medium for 8 h, washed with complete medium and PBS, and stained with FCP-1 (5 µM) in DPBS for 45 min. At the last 5-min incubation, a nucleus stain, DRAQ-5 (5 µM), was added to the solution mixture. Without washing, the cells were imaged by confocal fluorescence microscopy.
Figure 14:
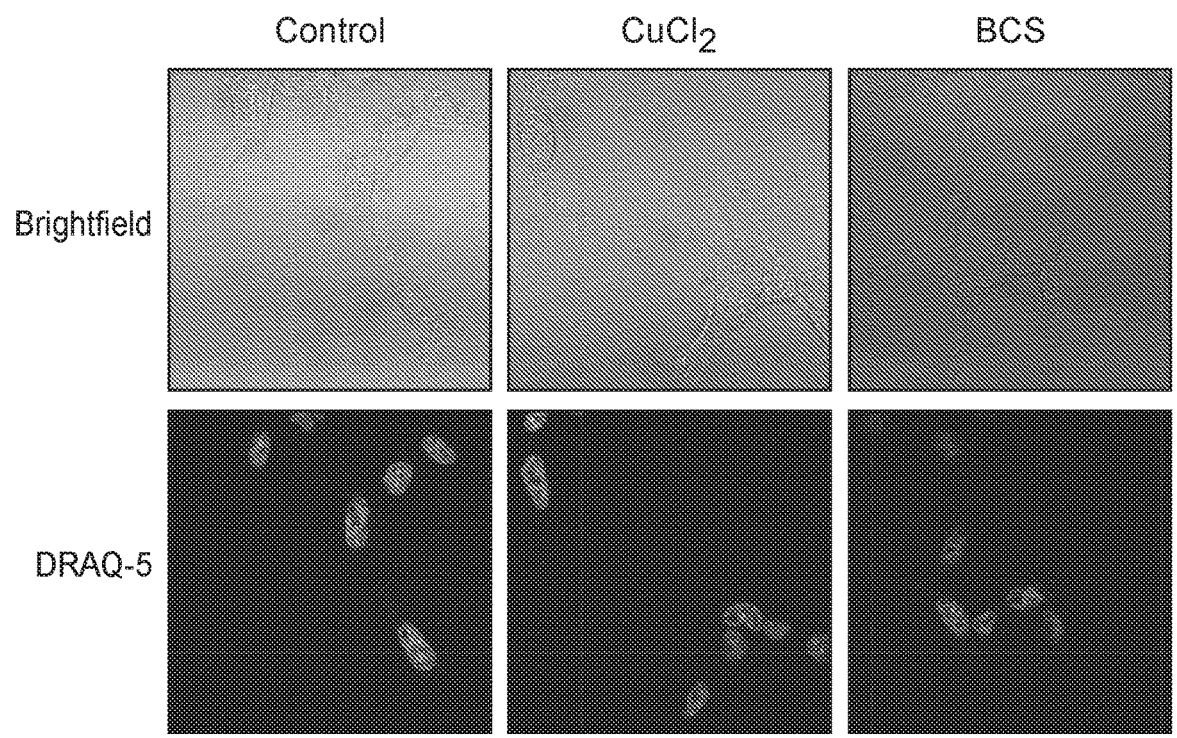
FIG. 14 shows confocal microscopy images of Ctrl$^{-/-}$ MEFs pretreated with solvent vehicle, CuCl$_2$ (100 µM) or BCS (500 µM) in complete medium for 8 h, washed with PBS and stained with FCP-1 (5 µM) in DPBS for 45 min. At the last 5-min incubation, a nucleus stain, DRAQ-5 (5 µM), was added to the solution mixture. Without washing, the cells were imaged by confocal fluorescence microscopy.
Figure 15:
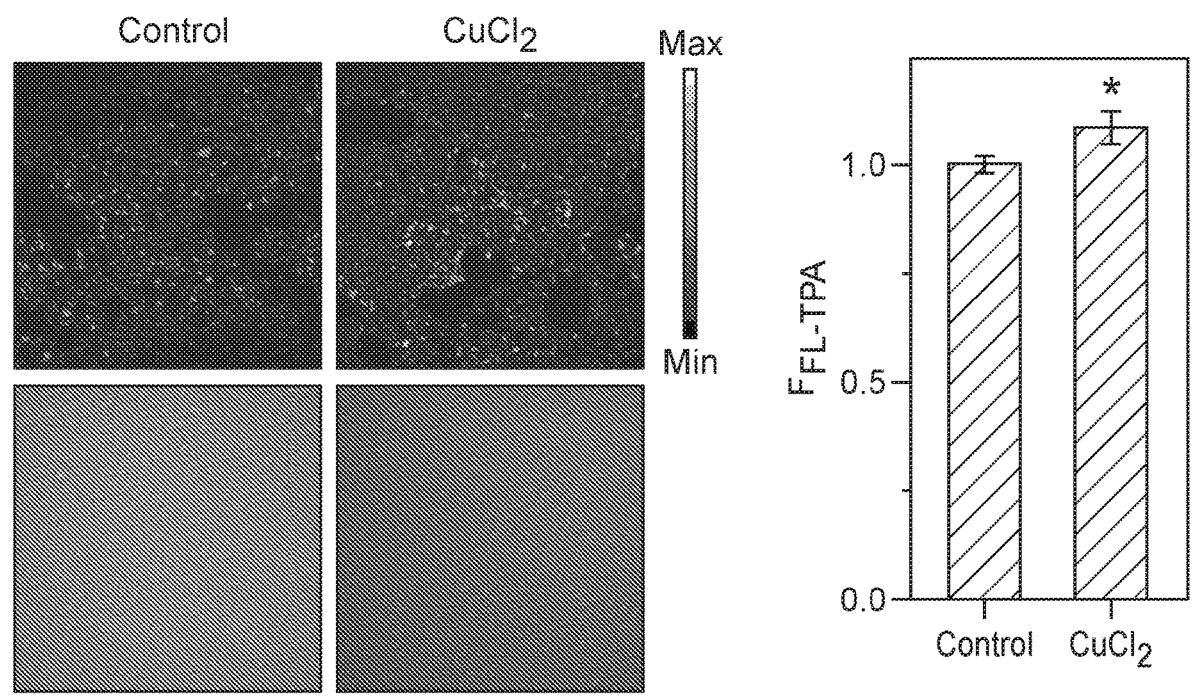
FIG. 15 shows Confocal microscopy images of HEK 293T cells pretreated with solvent vehicle or CuCl$_2$ (25 µM) in complete medium for 18 h, washed with PBS, stained with FL-TPA (5 µM) in DPBS for 45 min and imaged without washing. $\lambda_{ex}$=488 nm.

To further validate the capability of FCP-1 to monitor differential levels of labile Cu(I) in cells, $Ctr1^{+/+}$ MEFs incubated with varying concentrations of $CuCl_2$ exhibited a dose-dependent increase in the FCP-1 $F_{green}/F_{orange}$ ratio. In contrast, no statistically significant changes in $F_{green}/F_{orange}$ ratios were observed in $Ctr1^{-/-}$ MEFs incubated with $CuCl_2$ and then visualized with FCP-1 (FIGS. 12A-B). In meantime, the cellular viability was maintained, as confirmed with the nuclear stain DRAQ5 (FIG. 13-14). The difference of FCP-1 ratiometric fluorescence response to exogenous copper supplementation between the wildtype and Ctr1 knockout MEFs is consistent with inefficient copper uptake rather than changes in copper efflux, as treatment of Ctr1$^{-/-}$ MEFs with the membrane-impermeable copper chelator BCS resulted in a reduction in $F_{green}/F_{orange}$ ratio, similar to what is observed in Ctr1$^{+/+}$ MEFs (FIGS. 12A-B). Complementary ICP-MS measurements confirm that total copper levels in Ctr1$^{-/-}$ MEFs are lower than Ctr1$^{+/+}$ MEFs (FIG. 12C). The ratiometric response of FCP-1 provides the ability to distinguish between basal and decreased levels of labile Cu(I). Indeed, the control probe FL-TPA, which exhibits a "turn-on" fluorescence response without ratiometric self-calibration, was unable to distinguish differences in basal labile Cu(I) levels in Ctr1$^{+/+}$ MEFs and Ctr1$^{-/-}$ MEFs (FIGS. 12D-E), while being able to detect changes in labile copper with exogenous copper addition (FIG. 15). This result can be explained by potential differences in probe loading into the two MEF cell lines, showing the self-calibrating nature of the ratiometric probe FCP-1. The data demonstrate that FCP-1 can monitor basal levels of endogenous labile Cu(I) and depletion of such pools in response to reduced cellular copper uptake through either genetic or pharmacologic means.

Example 5

Figure 16:
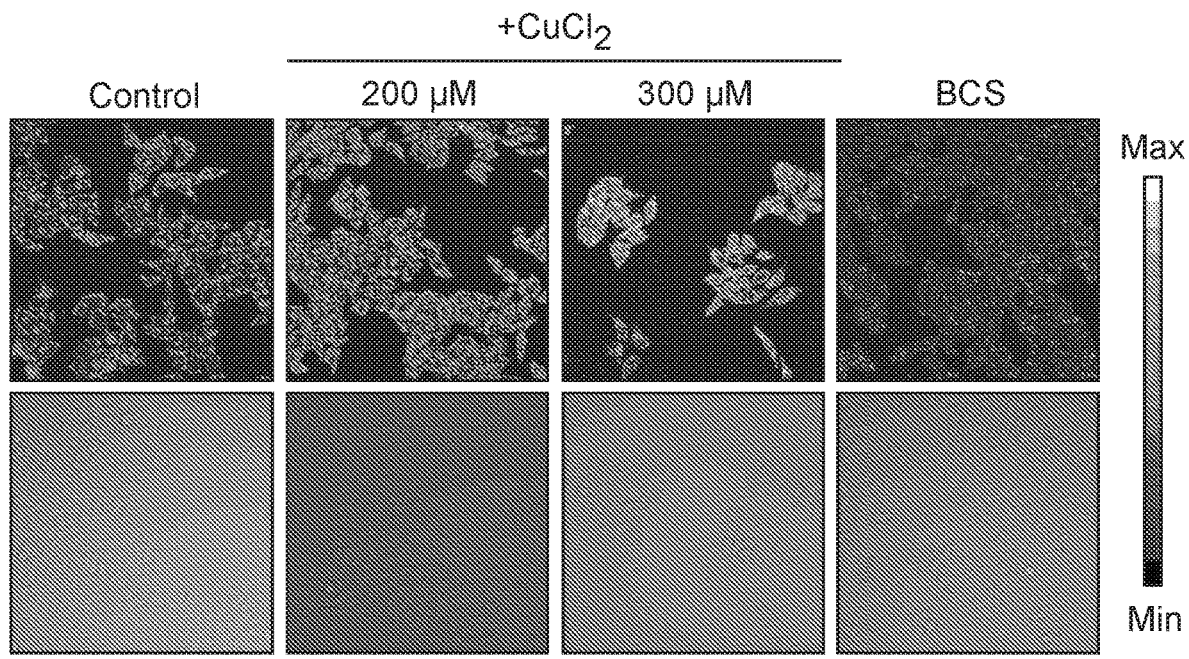
FIG. 16 shows how FCP-1 identifies changes in labile Cu(I) but not total copper levels in live cells under redox stress. Confocal fluorescence microscopy images of HeLa cells pretreated with (A) solvent control, CuCl$_2$ (200 or 300 µM), or BCS (100 µM) in complete medium for 18 h, or (B) solvent control, ascorbate (1 mM), or BSO (1 mM) in complete medium for 4 h. The cells were then washed with PBS, incubated with FCP-1 (5 µM) in DPBS for 45 min and imaged with $\lambda_{ex}$=458 nm. The bar charts show average cellular ratiometric FCP-1 emission, $F_{green}/F_{orange}$, determined from experiments performed in triplicate. (C) Total cellular $^{63}$Cu levels were determined by ICP-MS experiments (with normalization of different cell numbers by total cellular $^{31P}$ level). Error bars denote SD (n=3). *p<0.05, p<0.01 and *p<0.001 and show no change with either ascorbate or BSO treatment.
Figure 16:
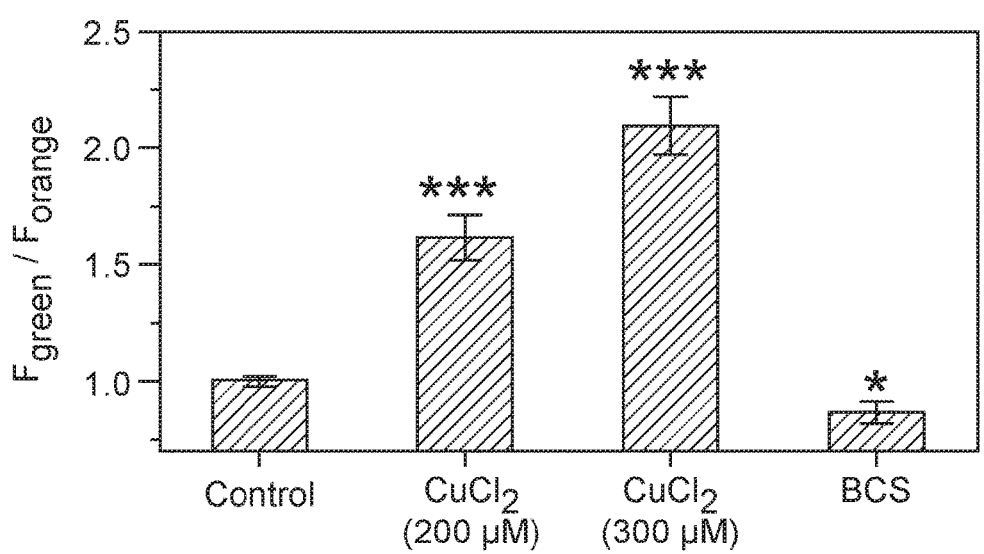
Figure 16:
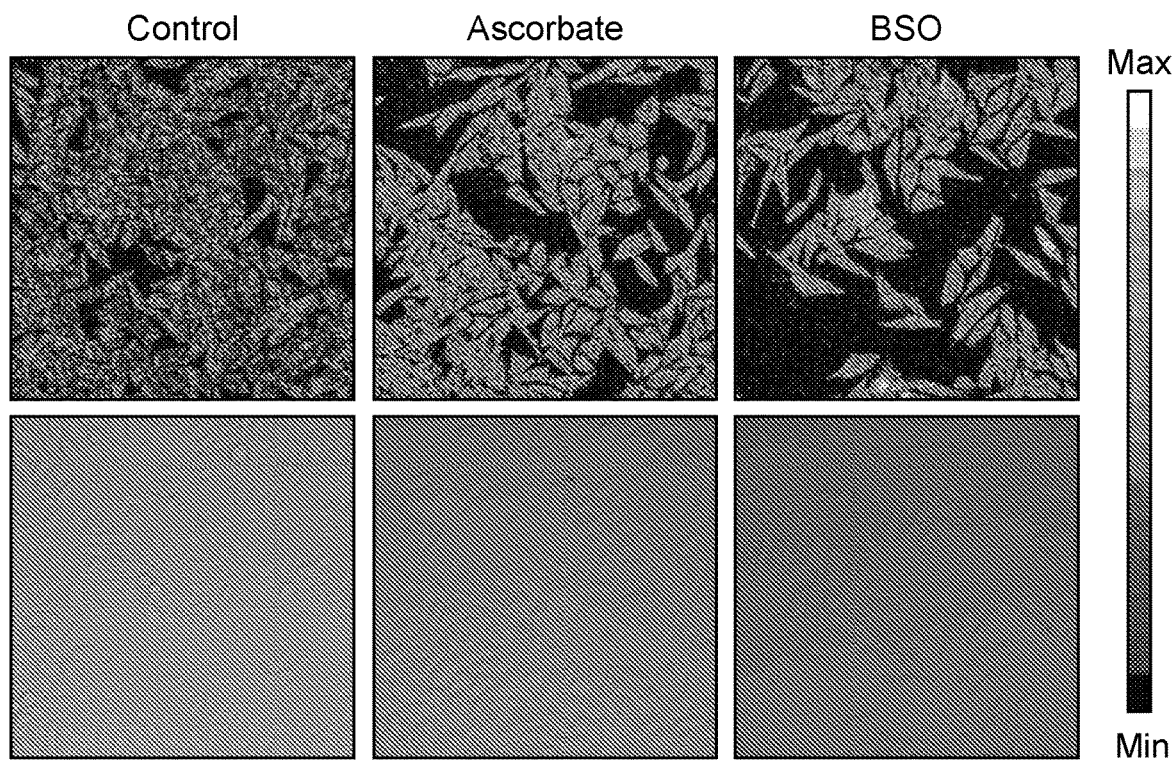
Figure 16:
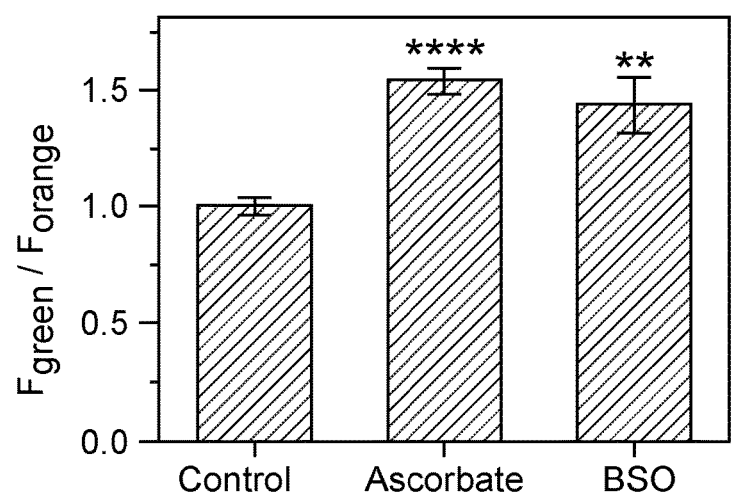
Figure 16:
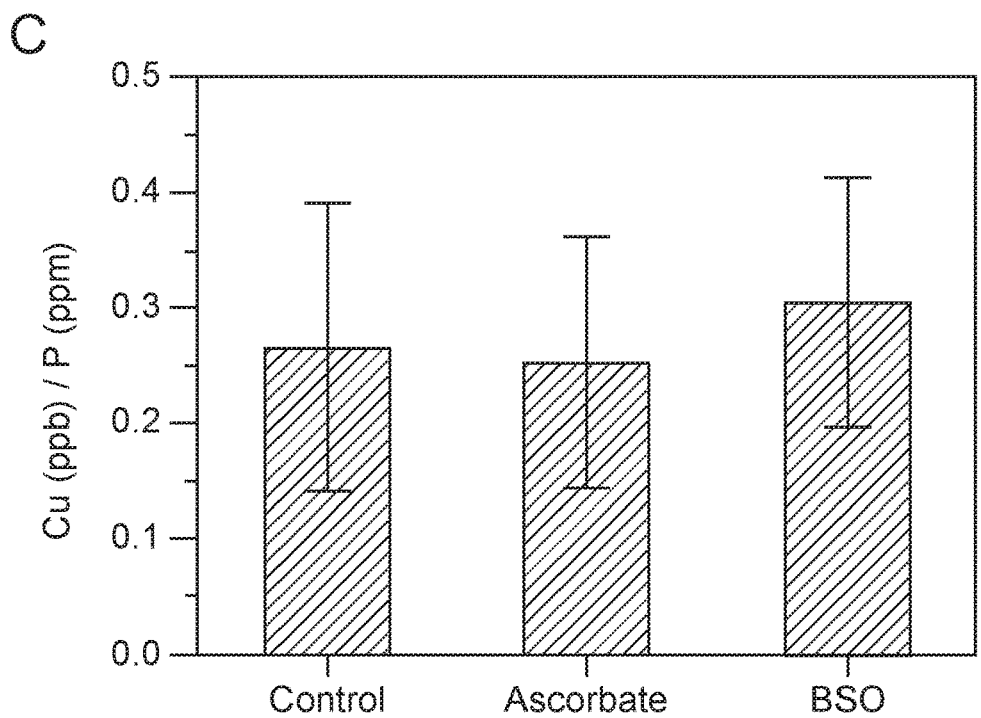

FCP-1 Identifies a Dynamic Change in Labile Cu(I) Versus Total Copper Pools in Living Cells Under Redox Stress In view of the oxidation state-specificity of FCP-1 toward Cu(I), the impact of cellular redox status on labile Cu(I) pools was examined First, the ability of FCP-1 to detect changes in labile Cu(I) levels in HeLa cells with CuCl$_2$ and BCS treatments was evaluated (FIG. 16A). The effect of addition of ascorbate, which is a powerful reducing agent, was monitored on intracellular labile Cu(I) pools. A statistically significant increase in FCP-1 $F_{green}/F_{orange}$ ratio was observed, suggesting an increase in labile Cu(I) levels in the ascorbate-treated cells compared to the control cells (FIG. 16B) (25). The accompanying ICP-MS measurements showed no changes in total copper levels in cells treated with ascorbate compared to vehicle controls (FIG. 16C).

Figure 17:
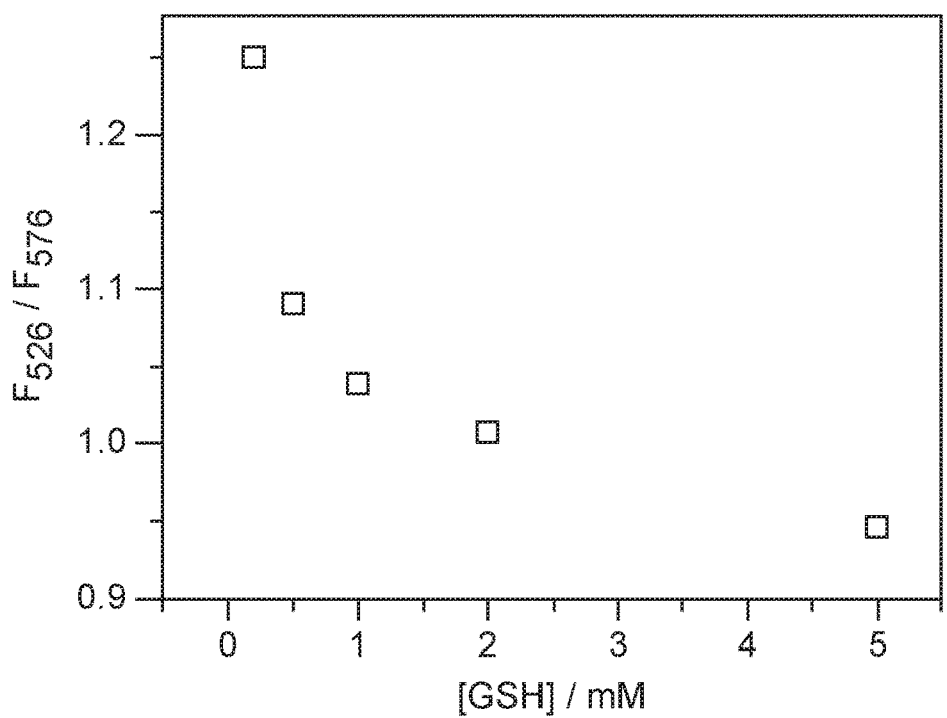
FIG. 17 shows $F_{526}/F_{576}$ of FCP-1 (5 µM) and Cu(I) (10 µM) in aqueous buffer solution (PBS containing 40 vol % PEG-400) with different concentrations of GSH after incubation for 15 min. $\lambda_{ex}$=458 nm.

With these results in hand, FCP-1 was utilized to explore potential connections between the maintenance of labile Cu(I) pools and endogenous central redox mediators in the cell. In this context, glutathione (GSH) is a naturally-occurring antioxidant and a small molecule that affects proper cellular redox status (67). The rate-determining step of GSH biosynthesis involves glutamate cysteine ligase (GCL), which can be inhibited by buthionine sulfoximine (BSO) (68). It was observed that the FCP-1 $F_{green}/F_{orange}$ ratio was higher in BSO-treated HeLa cells when compared to control cells (FIG. 16B) indicating an increase in labile Cu(I) levels when GSH synthesis is blocked. Total intracellular copper levels did not differ significantly between the BSO-pretreated cells and control cells as shown by ICP-MS (FIG. 16C), showing that the dynamic changes are in the labile Cu(I) pool rather than an overall increase or decrease in the total copper pool. Aqueous solutions of FCP-1 and Cu(I) were found to show higher $F_{526}/F_{576}$ ratios at lower GSH concentrations in vitro (FIG. 17).

REFERENCES

1. Lippard S J, Berg J M (1994) Principles of bioinorganic chemistry. University Science Books, Mill Valley, California
2. Ridge P G, Zhang Y, Gladyshev V N (2008) Comparative Genomic Analyses of Copper Transporters and Cuproproteomes Reveal Evolutionary Dynamics of Copper Utilization and Its Link to Oxygen. *PLOS ONE* 3(1):e1378.
3. Que E L, Domaille D W, Chang C J (2008) Metals in Neurobiology: Probing Their Chemistry and Biology with Molecular Imaging. *Chem Rev* 108(5):1517-1549.
4. Boal A K, Rosenzweig A C (2009) Structural Biology of Copper Trafficking. *Chem Rev* 109(10):4760-4779.
5. Brady D C, et al. (2014) Copper is required for oncogenic BRAF signalling and tumorigenesis. *Nature* 509(7501): 492-496.
6. Krishnamoorthy L, et al. (2016) Copper regulates cyclic-AMP-dependent lipolysis. *Nat Chem Biol* 12(8):586-592.
7. Banci L, et al. (2010) Affinity gradients drive copper to cellular destinations. *Nature* 465(7298):645-648.
8. Chang C J (2015) Searching for harmony in transition-metal signaling. *Nat Chem Biol* 11:744.
9. Schlief M L, Craig A M, Gitlin J D (2005) NMDA Receptor Activation Mediates Copper Homeostasis in Hippocampal Neurons. *J Neurosci* 25(1):239.
10. Dodani S C, et al. (2011) Calcium-dependent copper redistributions in neuronal cells revealed by a fluorescent copper sensor and X-ray fluorescence microscopy. *Proc Natl Acad Sci* 108(15):5980-5985.
11. Dodani S C, et al. (2014) Copper is an endogenous modulator of neural circuit spontaneous activity. *Proc Natl Acad Sci* 111(46):16280-16285.
12. Crabtree R H (1978) Copper (I): A possible olfactory binding site. *J Inorg Nucl Chem* 40(7):1453.
13. Duan X, et al. (2012) Crucial role of copper in detection of metal-coordinating odorants. *Proc Natl Acad Sci* 109 (9):3492.
14. Xiao T, et al. (2018) Copper regulates rest-activity cycles through the locus coeruleus-norepinephrine system. *Nat Chem Biol* 14(7):655-663.
15. Turski M L, et al. (2012) A Novel Role for Copper in Ras/Mitogen-Activated Protein Kinase Signaling. *Mol Cell Biol* 32(7):1284-1295.
16. Finkel T, Serrano M, Blasco M A (2007) The common biology of cancer and ageing. *Nature* 448:767.
17. Barnham K J, Bush A I (2014) Biological metals and metal-targeting compounds in major neurodegenerative diseases. *Chem Soc Rev* 43(19):6727-6749.
18. Kaler S G (2011) ATP7A-related copper transport diseases-emerging concepts and future trends. *Nat Rev Neurol* 7(1):15-29.
19. Burkhead J L, Gray L W, Lutsenko S (2011) Systems biology approach to Wilson's disease. *BioMetals* 24(3): 455-466.
20. Merle U, Schaefer M, Ferenci P, Stremmel W (2007) Clinical presentation, diagnosis and long-term outcome of Wilson's disease: a cohort study. *Gut* 56(1):115-120.
21. Huster D, et al. (2006) Consequences of Copper Accumulation in the Livers of the Atp7b−/− (Wilson Disease Gene) Knockout Mice. *Am J Pathol* 168(2):423-434.
22. Cotruvo J A, Aron A T, Ramos-Torres K M, Chang C J (2015) Synthetic fluorescent probes for studying copper in biological systems. *Chem Soc Rev* 44(13):4400-4414.
23. Carter K P, Young A M, Palmer A E (2014) Fluorescent Sensors for Measuring Metal Ions in Living Systems. *Chem Rev* 114(8):4564-4601.
24. Aron A T, Ramos-Torres K M, Cotruvo J A, Chang C J (2015) Recognition- and Reactivity-Based Fluorescent Probes for Studying Transition Metal Signaling in Living Systems. *Acc Chem Res* 48(8):2434-2442.

25. Fahrni C J (2013) Synthetic fluorescent probes for monovalent copper. *Curr Opin Chem Biol* 17(4):656-662.
26. Yang L, et al. (2005) Imaging of the intracellular topography of copper with a fluorescent sensor and by synchrotron x-ray fluorescence microscopy. *Proc Natl Acad Sci* 102(32):11179-11184.
27. Zeng L, Miller E W, Pralle A, Isacoff E Y, Chang C J (2006) A Selective Turn-On Fluorescent Sensor for Imaging Copper in Living Cells. *J Am Chem Soc* 128(1):10-11.
28. Taki M, Iyoshi S, Ojida A, Hamachi I, Yamamoto Y (2010) Development of Highly Sensitive Fluorescent Probes for Detection of Intracellular Copper(I) in Living Systems. *J Am Chem Soc* 132(17):5938-5939.
29. Dodani S C, Leary S C, Cobine P A, Winge D R, Chang C J (2011) A Targetable Fluorescent Sensor Reveals That Copper-Deficient SCO1 and SCO2 Patient Cells Prioritize Mitochondrial Copper Homeostasis. *J Am Chem Soc* 133(22):8606-8616.
30. Hirayama T, Bittner G C V de, Gray L W, Lutsenko S, Chang C J (2012) Near-infrared fluorescent sensor for in vivo copper imaging in a murine Wilson disease model. *Proc Natl Acad Sci* 109(7):2228-2233.
31. Domaille D W, Zeng L, Chang C J (2010) Visualizing Ascorbate-Triggered Release of Labile Copper within Living Cells using a Ratiometric Fluorescent Sensor. *J Am Chem Soc* 132(4):1194-1195.
32. Shen C, et al. (2016) A ratiometric fluorescent sensor for the mitochondrial copper pool. *Metallomics* 8(9):915-919.
33. Park S Y, et al. (2017) An endoplasmic reticulum-selective ratiometric fluorescent probe for imaging a copper pool. *Chem Commun* 53(32):4457-4460.
34. Lin W, Yuan L, Tan W, Feng J, Long L (2009) Construction of Fluorescent Probes Via Protection/Deprotection of Functional Groups: A Ratiometric Fluorescent Probe for Cu2+. *Chem-Eur J* 15(4):1030-1035.
35. Zhou Y, Wang F, Kim Y, Kim S-J, Yoon J (2009) Cu2+-Selective Ratiometric and "Off-On" Sensor Based on the Rhodamine Derivative Bearing Pyrene Group. *Org Lett* 11(19):4442-4445.
36. Zhou L, et al. (2014) Molecular Engineering of a TBET-Based Two-Photon Fluorescent Probe for Ratiometric Imaging of Living Cells and Tissues. *J Am Chem Soc* 136(28):9838-9841.
37. Giuffrida M L, et al. (2018) A New Ratiometric Lysosomal Copper(II) Fluorescent Probe To Map a Dynamic Metallome in Live Cells. *Inorg Chem* 57(5):2365-2368.
38. Biesemeier A, et al. (2016) Elemental mapping of Neuromelanin organelles of human Substantia Nigra: correlative ultrastructural and chemical analysis by analytical transmission electron microscopy and nano-secondary ion mass spectrometry. *J Neurochem* 138(2):339-353.
39. Heffern M C, et al. (2016) In vivo bioluminescence imaging reveals copper deficiency in a murine model of nonalcoholic fatty liver disease. *Proc Natl Acad Sci* 113(50):14219-14224.
40. Que E L, C hang C J (2010) Responsive magnetic resonance imaging contrast agents as chemical sensors for metals in biology and medicine. *Chem Soc Rev* 39(1):51-60.
41. Que E L, Chang C J (2006) A Smart Magnetic Resonance Contrast Agent for Selective Copper Sensing. *J Am Chem Soc* 128(50):15942-15943.
42. Que E L, et al. (2009) Copper-Responsive Magnetic Resonance Imaging Contrast Agents. *J Am Chem Soc* 131(24):8527-8536.
43. Ackerman C M, Lee S, Chang C J (2017) Analytical Methods for Imaging Metals in Biology: From Transition Metal Metabolism to Transition Metal Signaling. *Anal Chem* 89(1):22-41.
44. Hare D J, New E J, de Jonge M D, McColl G (2015) Imaging metals in biology: balancing sensitivity, selectivity and spatial resolution. *Chem Soc Rev* 44(17):5941-5958.
45. Konz I, Fernández B, Fernández M L, Pereiro R, Sanz-Medel A (2012) Laser ablation ICP-MS for quantitative biomedical applications. *Anal Bioanal Chem* 403(8):2113-2125.
46. Becker J S (2013) Imaging of metals in biological tissue by laser ablation inductively coupled plasma mass spectrometry (LAICPMS): state of the art and future developments. *J Mass Spectrom* 48(2):i-i.
47. Pozebon D, Scheffler G L, Dressler V L, Nunes M A G (2014) Review of the applications of laser ablation inductively coupled plasma mass spectrometry (LA-ICP-MS) to the analysis of biological samples. *J Anal At Spectrom* 29(12):2204-2228.
48. Hong-Hermesdorf A, et al. (2014) Subcellular metal imaging identifies dynamic sites of Cu accumulation in Chlamydomonas. *Nat Chem Biol* 10(12):1034-1042.
49. Fahrni C J (2007) Biological applications of X-ray fluorescence microscopy: exploring the subcellular topography and speciation of transition metals. *Bioinorg Chem Biocatal Biotransformation* 11(2):121-127.
50. James S A, et al. (2016) φXANES: In vivo imaging of metal-protein coordination environments. *Sci Rep* 6:20350.
51. Tsien R Y (1988) Fluorescence measurement and photochemical manipulation of cytosolic free calcium. *Trends Neurosci* 11(10):419-424.
52. Zlokarnik G, et al. (1998) Quantitation of Transcription and Clonal Selection of Single Living Cells with β-Lactamase as Reporter. *Science* 279(5347):84.
53. Minta A, Kao J P, Tsien R Y (1989) Fluorescent indicators for cytosolic calcium based on rhodamine and fluorescein chromophores. *J Biol Chem* 264(14):8171-8178.
54. Tsien R Y, Bacskai B J, Adams S R (1993) FRET for studying intracellular signalling. *Trends Cell Biol* 3(7):242-245.
55. Single-Molecule Fluorescence Resonance Energy Transfer (2001) *Methods* 25(1):78-86.
56. Yuan L, Lin W, Zheng K, Zhu S (2013) FRET-Based Small-Molecule Fluorescent Probes: Rational Design and Bioimaging Applications. *Acc Chem Res* 46(7):1462-1473.
57. Lee M H, Kim J S, Sessler J L (2015) Small molecule-based ratiometric fluorescence probes for cations, anions, and biomolecules. *Chem Soc Rev* 44(13):4185-4191.
58. Kunishita A, Ishimaru H, Nakashima S, Ogura T, Itoh S (2008) Reactivity of Mononuclear Alkylperoxo Copper (II) Complex. O—O Bond Cleavage and C—H Bond Activation. *J Am Chem Soc* 130(13):4244-4245.
59. Liu J J, Diaz D E, Quist D A, Karlin K D (2016) Copper(I)-Dioxygen Adducts and Copper Enzyme Mechanisms. *Isr J Chem* 56(9-10):738-755.
60. Zhou H-X, Rivas G, Minton A P (2008) Macromolecular Crowding and Confinement: Biochemical, Biophysical, and Potential Physiological Consequences. *Annu Rev Biophys* 37(1):375-397.
61. Nakano S, Miyoshi D, Sugimoto N (2014) Effects of Molecular Crowding on the Structures, Interactions, and Functions of Nucleic Acids. *Chem Rev* 114(5):2733-2758.

62. WILLIAMS R T, BRIDGES J W (1964) FLUORESCENCE OF SOLUTIONS: A REVIEW. *J Clin Pathol* 17(4):371-394.
63. Birch C S, Brasch N E, McCaddon A, Williams J H H (2009) A novel role for vitamin B12: Cobalamins are intracellular antioxidants in vitro. *Free Radic Biol Med* 47(2):184-188.
64. Feo C J D, Aller S G, Siluvai G S, Blackburn N J, Unger V M (2009) Three-dimensional structure of the human copper transporter hCTR1. *Proc Natl Acad Sci* 106(11): 4237-4242.
65. Lee J, Petris M J, Thiele D J (2002) Characterization of Mouse Embryonic Cells Deficient in the Ctr1 High Affinity Copper Transporter: IDENTIFICATION OF A Ctr1-INDEPENDENT COPPER TRANSPORT SYSTEM. *J Biol Chem* 277(43):40253-40259.
66. Maryon E B, Molloy S A, Ivy K, Yu H, Kaplan J H (2013) Rate and regulation of copper transport by human copper transporter 1 (hCTR1). *J Biol Chem* 288(25): 18035-18046.
67. Traverso N, et al. (2013) Role of Glutathione in Cancer Progression and Chemoresistance % J Oxidative Medicine and Cellular Longevity. 2013:10.
68. Marí M, Bai J, Cederbaum A I (2002) Toxicity by pyruvate in HepG2 cells depleted of glutathione: role of mitochondria. *Free Radic Biol Med* 32(1):73-83.
69. Morgan M T, Nguyen L A H, Hancock H L, Fahrni C J (2017) Glutathione limits aquacopper(I) to sub-femtomolar concentrations through cooperative assembly of a tetranuclear cluster. *J Biol Chem*: jbc.M117.817452.
70. Hatori Y, et al. (2016) Neuronal differentiation is associated with a redox-regulated increase of copper flow to the secretory pathway. *Nat Commun* 7:10640.
71. Hatori Y, Clasen S, Hasan N M, Barry A N, Lutsenko S (2012) Functional Partnership of the Copper Export Machinery and Glutathione Balance in Human Cells. *J Biol Chem* 287(32):26678-26687.
72. Jiang J, et al. (2002) Contribution of Glutathione and Metallothioneins to Protection against Copper Toxicity and Redox Cycling: Quantitative Analysis Using MT+/+ and MT-/- Mouse Lung Fibroblast Cells. *Chem Res Toxicol* 15(8):1080-1087.
73. Couto N, Wood J, Barber J (2016) The role of glutathione reductase and related enzymes on cellular redox homoeostasis network. *Free Radic Biol Med* 95:27-42.
74. Gorrini C, Harris I S, Mak T W (2013) Modulation of oxidative stress as an anticancer strategy. *Nat Rev Drug Discov* 12:931.
75. DeNicola G M, et al. (2011) Oncogene-induced Nrf2 transcription promotes ROS detoxification and tumorigenesis. *Nature* 475:106.

ADDITIONAL REFERENCES

1. Adamczyk M, Grote J, Moore J A (1999) Chemoenzymatic Synthesis of 3'-O-(Carboxyalkyl)fluorescein Labels. *Bioconjug Chem* 10(3):544-547.
2. Komatsu K, Kikuchi K, Kojima H, Urano Y, Nagano T (2005) Selective Zinc Sensor Molecules with Various Affinities for Zn2+, Revealing Dynamics and Regional Distribution of Synaptically Released Zn2+ in Hippocampal Slices. *J Am Chem Soc* 127(29):10197-10204.
3. Zhang P, et al. (2015) A logic gate-based fluorescent sensor for detecting H2S and NO in aqueous media and inside live cells. *Chem Commun* 51(21):4414-4416.
4. Gardecki J A, Maroncelli M (1998) Set of Secondary Emission Standards for Calibration of the Spectral Responsivity in Emission Spectroscopy. *Appl Spectrosc* 52(9):1179-1189.

What is claimed is:

1. A compound of the formula (I):

$$A-X1-E-X2-D \qquad (I)$$

wherein:

A is a Förster resonance energy transfer (FRET) acceptor group,

D is a FRET donor group,

E is a Cu(I)-coordinating group,

X1 and X2 are linking groups.

2. The compound of claim 1, wherein X1, X2, or both X1 and X2 are cleavable by Cu(I).

3. The compound of claim 2, wherein X1 and not X2 is cleavable by Cu(I) or wherein X2 and not X1 is cleavable by Cu(I).

4. The compound of claim 2, wherein at least one of the A-X1 moiety and the X2-D moiety comprises a C—O bond cleavable by Cu(I).

5. The compound of claim 4, wherein the compound comprises the structure of formula (II):

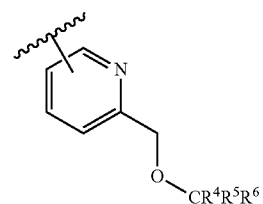

wherein a C—O group of formula (II) is cleavable by Cu(I), wherein $R^4$, $R^5$, and $R^6$ are each independently selected from H or a hydrocarbon group.

6. The compound of claim 5, wherein the compound comprises the structure of formula (III):

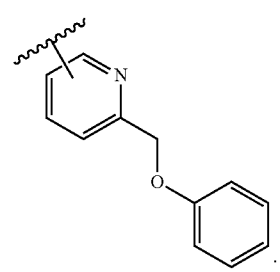

7. The compound of claim 2, wherein at least one of the A-X1 moiety and the X2-D moiety comprises a C—N bond cleavable by Cu(I).

8. The compound of claim 1, wherein E has a formula selected from:

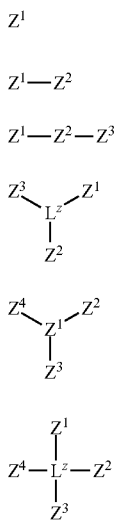

wherein each Z is a coordination group,
wherein $L^z$ is a linker,
wherein E is a tridentate or tetradentate group.

9. The compound of claim 8, wherein each Z is independently selected from:

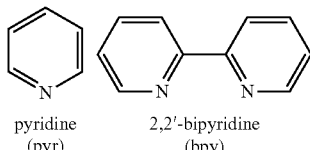

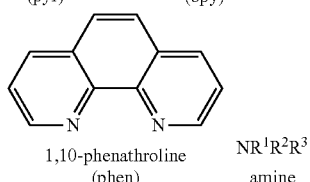

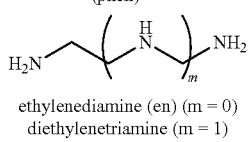

formula (X)

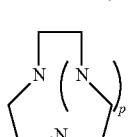

formula (XI)

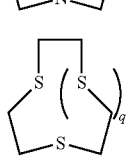

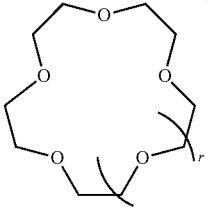

a functionalized thioether, and derivatives and homologs thereof,
wherein m is 0 or 1,
wherein n is 0 or 1,
wherein p is 1 or 2,
wherein q is 1 or 2,
wherein r is 1 or 2,
wherein each of $R^1$, $R^2$, and $R^3$ are independently selected from H and an alkyl group.

10. The compound of claim 8, wherein E has the formula (VIII).

11. The compound of claim 10, wherein $Z^1$ is $NR^1R^2R^3$ and wherein each of $R^1$, $R^2$, and $R^3$ is an alkyl group.

12. The compound of claim 11, wherein $Z^2$, $Z^3$, and $Z^4$ are each comprise a pyridine group.

13. The compound of claim 12, wherein E comprises the structure (XII):

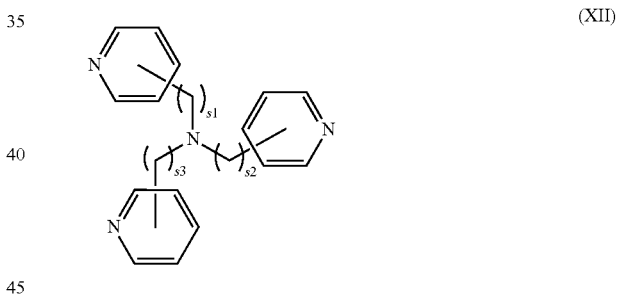

wherein s1, s2, and s3 are each independently selected from 0, 1, 2, 3, 4, and 5.

14. The compound of claim 13, wherein E comprises the structure (XIII):

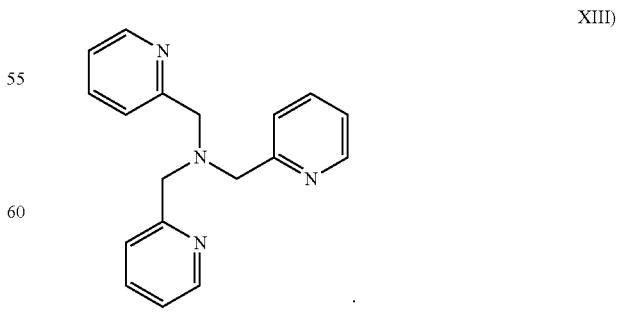

15. The compound of claim 14, wherein the composition comprises the structure (XIV):

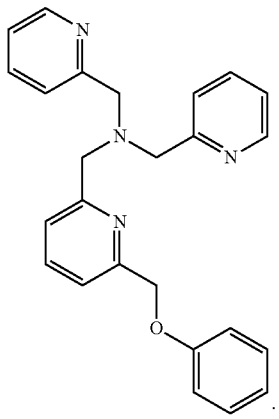

(XIV)

16. The composition of claim 8, wherein:
a) E has the formula (VIII) or (IX) and each Z comprises a pyridine group;
b) wherein E has the formula (V), (VI) or (VII) and $Z^1$ is a bidentate group;
c) wherein E has the formula (V) and wherein $Z^1$ and $Z^2$ are each a bidentate group;
d) wherein E has the formula (VI) or (VII) or (VIII), or (IX), and wherein at least one Z comprises $NR^1R^2R^3$; or
e) wherein E has the formula (IV) or (V), and wherein $Z^1$ has the formula (X), (XI), 15-crown-5, 18-crown-6, or a functionalized thioether.

17. The compound of claim 1, wherein A comprises a small molecule dye group, a fluorescent protein group, or a quantum dot.

18. The compound of claim 1, wherein A has an excitation maximum between 500 nm and 600 nm, and wherein D has an excitation maximum between 450 nm and 525 nm.

19. The compound of claim 1, wherein D comprises a small molecule dye group, a fluorescein group, a fluorescent protein group, or a quantum dot.

20. A method of detecting Cu(I) in a living cell, the method comprising:
a) contacting the cell with a compound according to claim 1; and
b) detecting ratiometric emission from the probe.

* * * * *